(12) United States Patent
Guan et al.

(10) Patent No.: US 8,754,058 B2
(45) Date of Patent: Jun. 17, 2014

(54) INHIBITORS OF FAM3B GENE, INHIBITOR COMPOSITIONS, INHIBITING METHODS AND APPLICATIONS OF INHIBITORS IN PREPARING PHARMACEUTICALS

(75) Inventors: Youfei Guan, Beijing (CN); Zicai Liang, Beijing (CN)

(73) Assignee: Suzhou Ribo Life Science Company, Ltd., Jiangsu (CN)

( * ) Notice: Subject to any disclaimer, the term of this patent is extended or adjusted under 35 U.S.C. 154(b) by 0 days.

(21) Appl. No.: 13/498,717

(22) PCT Filed: Nov. 26, 2010

(86) PCT No.: PCT/CN2010/079187
§ 371 (c)(1),
(2), (4) Date: Nov. 7, 2012

(87) PCT Pub. No.: WO2011/038700
PCT Pub. Date: Apr. 7, 2011

(65) Prior Publication Data
US 2013/0046006 A1 Feb. 21, 2013

(30) Foreign Application Priority Data
Sep. 29, 2009 (CN) .......................... 2009 1 0178454

(51) Int. Cl.
*C12N 15/11* (2006.01)
*C12Q 1/68* (2006.01)

(52) U.S. Cl.
USPC ........................................ 514/44 A; 435/6.1

(58) Field of Classification Search
None
See application file for complete search history.

(56) References Cited

U.S. PATENT DOCUMENTS

2005/0246794 A1* 11/2005 Khvorova et al. ............ 800/286
2006/0275794 A1* 12/2006 Carrino et al. .................... 435/6

OTHER PUBLICATIONS

Wang et al, Mechanisms of Glucose-Induced Expression of Pancreatic-Derived Factor in Pancreatic b-Cells, Endocrinology, 2008, 149, 2:672-680.*
International Search Report for Application No. PCT/CN2010/079187 dated Mar. 10, 2011.
Wang Ou-mei, et al., "Progresses in research of FAM3 family", Chinese Bulletin of Life Sciences, vol. 21, No. 2, Apr. 30, 2009, pp. 280-285 (ISSN 1004-0374).
Zhu Yuan, et al., "Cloning, Expression, and Initial Characterization of a Novel Cytokine-like Gene Family", Genomics, vol. 80, No. 2, Aug. 31, 2002, pp. 144-150.
Yuan Yang, et al., "PANDER and β cell apoptosis", Intern J. Endocrinol Metab, vol. 27, No. 4, Jul. 31, 2007, pp. 259-260, 266 (ISSN 1673-4157).
Cao Xiaopei, et al., "Pancreatic-Derived Factor (FAM3B), a Novel Islet Cytokine, Induces Apoptosis of Insulin-Secreting β-Cells", Diabetes, vol. 52, No. 9, Sep. 30, 2003, pp. 2296-2303.
Yang Jichun, et al., "Structure-Function Studies of PANDER, an Islet Specific Cytokine Inducing Cell Death of Insulin-Secreting β Cells", Biochemistry, vol. 44, No. 34, Aug. 31, 2005, pp. 11342-11352.

* cited by examiner

*Primary Examiner* — Tracy Vivlemore
*Assistant Examiner* — Kate Poliakova-Georgantas
(74) *Attorney, Agent, or Firm* — Smith, Gambrell & Russell LLP

(57) ABSTRACT

Inhibitors that can inhibit expression of FAM3B gene to reduce the levels of expression products, or can combine the expression products to reduce the activity of promoting lipid synthesis of FAM3B gene product are provided, wherein the inhibitors are one or more inhibitors selected from the group consisting of small interfering RNAs, antisense oligonucleotides, antibodies against FAM3B proteins and active organic compounds. Cells, vectors or inhibitor compositions, comprising such inhibitors, methods for inhibiting expression of FAM3B gene or inhibiting the activity of promoting lipid synthesis of FAM3B gene product using the inhibitors are provided. Methods for treating diseases mediated by expression of FAM3B gene using such inhibitors and uses of the inhibitors in preparing pharmaceuticals for preventing and/or treating the disease mediated by FAM3B gene expression are also provided.

Figure 1:
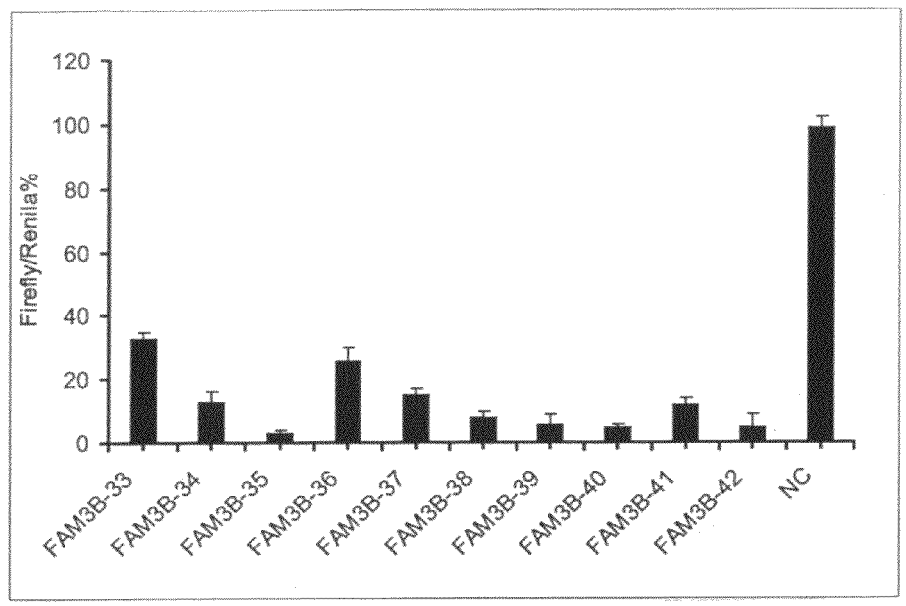

8 Claims, 6 Drawing Sheets

INHIBITORS OF FAM3B GENE, INHIBITOR COMPOSITIONS, INHIBITING METHODS AND APPLICATIONS OF INHIBITORS IN PREPARING PHARMACEUTICALS

SEQUENCE LISTING

The instant application contains a Sequence Listing which has been submitted in ASCII format via EFS-Web and is hereby incorporated by reference in its entirety. Said ASCII copy, created on Jun. 18, 2012, is named 03451602.txt and is 33,312 bytes in size.

TECHNICAL FIELD

The present invention relates to the inhibitors of FAM3B gene, cells, vectors and composition as well as inhibiting methods and methods for preventing and/or treating diseases and the uses of the inhibitor in preparing pharmaceuticals, more exactly, the present invention involves a inhibitor of FAM3B gene, cells comprising this inhibitor, vectors comprising this inhibitor, inhibitor compositions comprising this inhibitor, methods for inhibiting FAM3B gene expression or for inhibiting the activity of promoting lipid production of FAM3B gene product, methods for preventing and/or treating on the diseases mediated by FAM3B gene expression, as well as the uses of the inhibitor in preparing the pharmaceuticals for preventing and/or treating the diseases medicated by FAM3B gene expression.

BACKGROUND ART

Hepatic adipose infiltration is also termed as hepatic adipose degeneration, which refers to the lesions due to excessive lipopexia in hepatic cells induced by various kinds of reasons. It can be termed as hepatic adipose infiltration when fatty content is higher than 5% of the weight of liver (wet weight) (it can be as high as 40-50% at the most) or higher than 30% of the liver parenchyma in histology. Hepatic adipose infiltration may be induced by various kinds of diseases and reasons, the most common causes include obesity, alcoholism and diabetes, and further include nutritional disturbance, drug poisoning, pregnancy and the like. With continuous improvements in living standard of people, changes in diets and life style, the incidence rate of hepatic adipose infiltration has increased yearly and reached 10% of the average population, and it can be as high as 50-60% in specific populations with obesity, alcohol addict or diabetes. It is previously proposed that hepatic adipose infiltration is a benign lesion and it progresses slowly. However, it has been found in recent years that hepatic fibrosis is found about 25% of the patients and 1.5-8% of the patients may develop into hepatic cirrhosis. While 20% of the patients suffering from non-alcoholic fatty liver may develop into hepatic cirrhosis, 30-40% of them die of liver related diseases, and some of them may suffer from sub-acute hepatic failure and liver cancer. Therefore, prevention and treatments on hepatic adipose infiltration are very important for preventing progression of chronic liver disease and improving prognosis.

Currently, effective drugs are still unavailable for hepatic adipose infiltration, and the clinical practices still focus on removal of etiological factors, active treatments on primary diseases and maintenance of reasonable dietary regimen, while drugs only play adjunctive roles. The common drugs mainly focus on blood fat reduction, protection over hepatic cells and the like aspects, and effective therapeutic methods directly taking effects on hepatic lipidoses are still vacant.

On the other hand, with the improvements in living standard and the changes in diet constitution of people as well as the acceleration of aging of the society, the incidence rate of hyperlipemia has continuously increased and the hyperlipemia becomes a common and multiple disease. It has been investigated in previous studies that about 90 million people in our country suffer from hyperlipemia. Hyperlipemia has become a common disease in middle-aged and senile people, while various cardiovascular and cerebrovascular diseases induced by hyperlipemia have become a major cause threatening the lives of middle aged and senile people.

Blood fats mainly refer to cholesterol and triglyceride in serum. Hyperlipemia is a disease in which plasma levels of cholesterol and (or) triglyceride increase due to various kinds of reasons, and it is the pathological basis for inducing and aggravating artherosclerosis and an independent risk factor leading to artherosclerosis, angina, myocardial infarction, cerbral infarction, renal impairments and the like diseases of arterial embolism. Generally, hyperlipemia can be simply classified into hypercholesteremia, hypertriglyceridemia and mixed hyperlipemia. The diets of Chinese people are characterized by high sugar and low fat, and it has been investigated that sugar accounts for 76-79% of the gross calorific value, but fats only account for 8.4-10.6%, while the incidence rate of hyperlipemia is as high as 11%, and endogenous hypertriglyceridemia is the most common one. Drinking alcohol also has significant effects on plasma triglyceride level. In the sensitive individuals, even drinking alcohol at moderate amount may lead to hypertriglyceridemia. Alcohol can increase the synthesis rate of lipids in vivo, reduce the proportion of oxidized fatty acids and increase the proportion of esterified fatty acids. Moreover, alcohol can also reduce the activity of lipoproteinesterase and slow down the catabolism of triglyceride.

Blood fat is an important substance in human body, and plays many important roles, however, it can not exceed a certain level. Once blood fat is excessive, "dense blood" may be caused, and it will deposit on vessel wall and forms atherosclerotic plaques, and vessel wall is thickened, and the endangium becomes rough, and the lumen becomes narrow, thus it may lead to forming of thrombus or even blocking up of the lumen. If it takes place in coronary artery, it may lead to insufficient myocardial blood-supply, and heart-stroke or even myocardial infarction may happened; if it takes place in kidney, it may lead to renal arterial sclerosis and renal failure. Furthermore, hyperlipemia may lead to hypertension, and cause gallstone and pancreatitis, and aggravate hepatitis and the like diseases. Recent studies have shown that hypertriglyceridemia is an independent risk factor for coronary heart disease. Hypertriglyceridemia is directly related to death due to coronary heart disease or cardiovascular events (angina and myocardial infarction), or directly related when low HDL-cholesterol level is concurrent, or this correlation is reinforced when low HDL-cholesterol level is concurrent. Hypertriglyceridemia is the manifestation for abnormal lipoprotein metabolism, which is always concurrent with decrease in HDL level and increase in of small and dense LDL level. Small and dense LDL has strong effects in inducing artherosclerosis. Furthermore, hypertriglyceridemia is always concurrent with hyperinsulinemia, insulin resistance and hypercoagulabale state. Extremely high concentration of TG may further lead to acute pancreatitis.

Increase in blood fat is a slow process. Regulations on blood fat particularly elimination of the adverse effects of blood fat also require a continuous process, therefore, patients should select blood fat reducing drugs with significant therapeutic efficacy and mild toxic and side effects according to their different pathogenetic conditions. Control over hyperlipemia normally requires a long period or even all the life, and the expense is relatively high, and all of the currently available blood-fat reducing drugs have certain side effects. The common blood-fat reducing drugs now include statins, fibrates, chelating agents of cholic acid, nicotinic acid and other blood-fat reducing drugs. Treatments on hypertriglyceridemia are mainly based on drugs, and traditional Chinese drugs for blood-fat reducing have played important roles in reducing triglyceride, for example, the fourth generation of Jiangzhining granules of Junshan has been widely used in clinical practice since its therapeutic efficacy is accurate and the side effects are mild.

In recent years, people have made great efforts in studying and developing RNAi drugs, and RNAi drugs have shown extremely tremendous prospective in genetic diseases, tumors and other helpless diseases for human. RNAi (RNA interference) is a sequence-specific post-transcriptional gene silencing induced by double-strand RNA whose sequence is homologous to the target gene. siRNAs (small interfering RNAs) or small RNAs are RNA fragments with length of 19-23 nucleotides, and these fragments have been confirmed to be essential for RNA interference. siRNA forms RNA-induced silencing complex (RISC) with corresponding endogenous enzymes and proteins, and the sense strand of the double-strand siRNA is excluded from the complex during RNA interference, while the antisense strand directs the RISC to bind to corresponding site in the target mRNA, subsequently the target mRNA is degraded by ribonuclease III in the complex and thus the expression of the target gene is shut off. The phenomenon of RNA interference can not only provide a economical, rapid and efficient technical approach to inhibit gene expression, but also open new ideas for gene function determination, signaling pathway of cells, gene therapy and the like aspects. In comparison to traditional small molecule drugs and antibodies, RNAi therapy has the advantages as followed: (1) the process from the target to the drug is significantly shortened by reasonably designing drugs according to the sequence of the target gene; (2) the synthetic routes of RNAi drugs are almost identical; (3) RNAi therapy can be used target any gene, including non-drug and non-protein genes; (4) RNAi drugs are highly specific. Due to the advantages as mentioned above, many pharmaceutical companies have begun to develop RNAi drugs. siRNA drugs for hepatic adipose infiltration and hyperlipemia are still not available now all over the world, therefore, the application of siRNA in developing drugs for hepatic adipose infiltration and hyperlipemia will bring about significant influences on prevention and treatments on patients with hepatic adipose infiltration and hyperlipemia.

CONTENTS OF THE INVENTION

FAM3B factor is a cytokine specifically and highly expressed in islet β cells of pancreatic gland. Human FAM3B gene is located in the chromosome 21q22 and comprises at least eight exons, and it encodes a protein comprised of 235 amino acids. It is firstly cloned by a scientist in USA in 2002, and FAM3B is a new cytokine that may take effects during the pathological and physiological processes of diabetes.

The inventors carried out thorough studies on FAM3B factor during the investigations on pathological process of diabetes, and they surprisingly found that FAM3B gene showed dispersed expression in liver besides its potential functions in pathological and physiological processes of diabetes, indicating that FAM3B gene may function in the regulations on hepatic functions.

Therefore, the inventors carried out further investigations on FAM3B gene, and after treating wild-type mice with the adenovirus carrying FAM3B gene, it can be found that obvious steatosis can be detected in their livers, and the oil red staining of the hepatic sections showed lipid accumulation in large amount, the contents of triglyceride and cholesterol ester significantly increased in the hepatic tissues. Furthermore, FAM3B over-expression in the hepatic cell line increased the accumulation of neutral fats in hepatic cells. Therefore, it can be found that FAM3B factor may be involved in the formation of hepatic adipose infiltration and FAM3B gene may be the key factor for preventing and/or treating hepatic adipose infiltration.

On the other hand, mucous membrane of small intestine can synthesize large amount of triglyceride from monoglyceride after fat digestion and absorption. Both the food fats absorbed from intestinal tract and the fats synthesized in liver as well as the depot fats mobilized from adipose tissues have to be transported to other tissues by blood circulation. Triglyceride content in blood is directly related to fat absorption and synthesis in small intestine. Previous studies have found that FAM3B factor is expressed in small intestine, thus the inventors carried out thorough studies on the correlation between FAM3B gene in small intestine and triglyceride content in blood. The results showed that the expression level of FAM3B gene in the mice fed with high-fat feeds is higher than that in normal mice, and the triglyceride content in blood is also higher than that in normal mice. The triglyceride content in blood is significantly reduced by inhibiting the expression of FAM3B gene in small intestine with small interfering RNA. It can be found that FAM3B factor may be involved in the absorption/synthesis of triglyceride in small intestine, therefore, FAM3B gene may be a key factor for hyperlipemia and the inhibitor for FAM3B gene can be used to prevent/treat hyperlipemia.

Based on the findings as mentioned above, the inventors finished the present invention.

The first object of the present invention is to provide the inhibitor for FAM3B gene.

The second object of the present invention is to provide a cell comprising the inhibitor.

The third object of the present invention is to provide a vector comprising the inhibitor.

The fourth object of the present invention is to provide an inhibitor composition comprising the inhibitor.

The fifth object of the present invention is to provide a method for inhibiting FAM3B gene expression or for inhibiting the activity of promoting lipid production of FAM3B gene product.

The sixth object of the present invention is to provide a method for preventing and/or treating the disease mediated by FAM3B gene expression.

The seventh object of the present invention is to provide the uses of the inhibitor in preparing the pharmaceuticals for preventing and/or the disease mediated by FAM3B gene expression.

To achieve the first object of the present invention, the present invention provided a inhibitor, wherein, the inhibitor is capable of inhibiting the expression of FAM3B gene to reduce the level of FAM3B gene expression product; or the inhibitor is capable of binding to the expression product of FAM3B gene to reduce the activity of promoting lipid production of the FAM3B gene product.

To achieve the second object of the present invention, the present invention further provided a cell, wherein, the cell comprises the inhibitor provided by the present invention.

To achieve the third object of the present invention, the present invention further provided a vector, wherein, the vector comprises the inhibitor provided by the present invention.

To achieve the fourth object of the present invention, the present invention further provided a inhibitor composition, wherein, the inhibitor composition comprises the inhibitor provided by the present invention as the active ingredient.

To achieve the fifth object of the present invention, the present invention further provided a method for inhibiting FAM3B gene expression or for inhibiting the activity of promoting lipid production of FAM3B gene product, wherein the method comprises using the inhibitor or the inhibitor composition provided by the present invention to reduce the expression product level of FAM3B gene; or to reduce the activity of promoting lipid production of the FAM3B gene product.

To achieve the sixth object of the present invention, the present invention further provided a method for preventing and/or treating the disease mediated by FAM3B gene expression, wherein, the method comprises inhibiting FAM3B gene expression in patients to reduce the level of FAM3B gene expression product; or reducing the activity of promoting lipid production of the FAM3B gene product.

To achieve the seventh object of the present invention, the present invention further provided the uses of the inhibitor in preparing the pharmaceuticals for preventing and/or the disease mediated by FAM3B gene expression.

The present invention revealed the important functions of FAM3B gene in the diseases mediated by FAM3B gene expression and thus provided a effective approach for preventing and/or treating the diseases mediated by FAM3B gene expression (such as hepatic adipose infiltration and the diseases induced by hyperlipemia).

DESCRIPTIONS OF THE DRAWINGS

FIG. 1 showed the results of the in vitro screening for active targets in FAM3B by ten mouse-derived small interfering RNA provided in the present invention.

Figure 2:
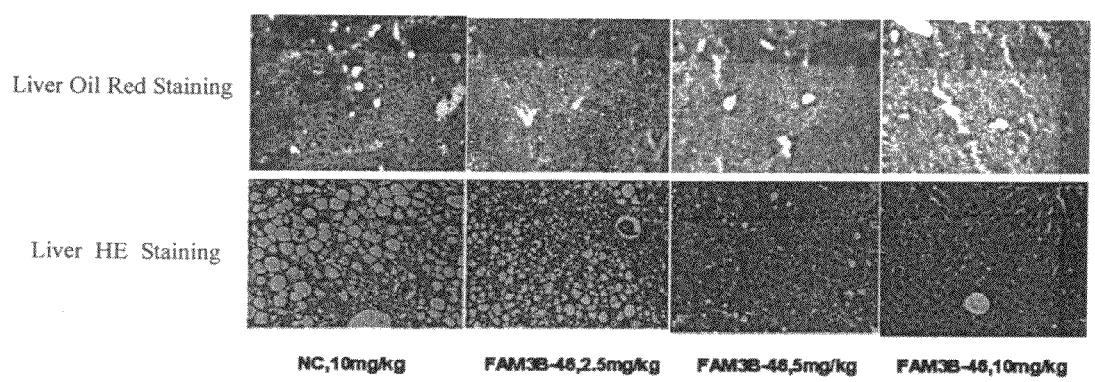

FIG. 2 showed the oil red O and HE staining results of hepatic steatosis degree of the mice after intravenous administration with sample of FAM3B-46 provided in the present invention.

Figure 3:
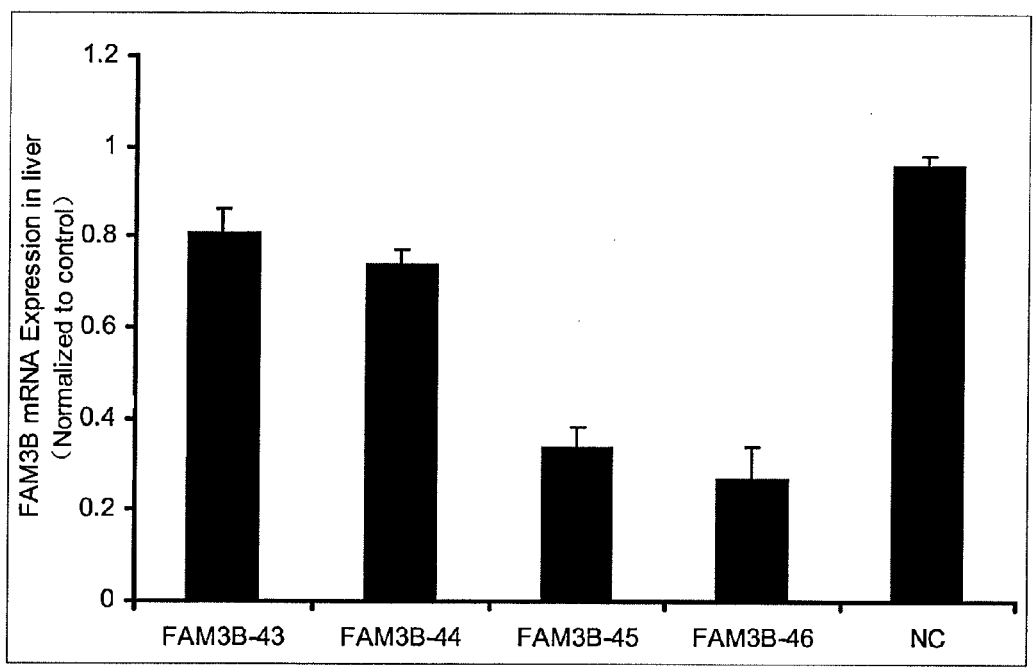

FIG. 3 showed the detection for the inhibitory effects of samples of FAM3B-43 to FAM3B-46 provided by the present invention on mRNA expression of FAM3B in the livers of mice.

Figure 4:
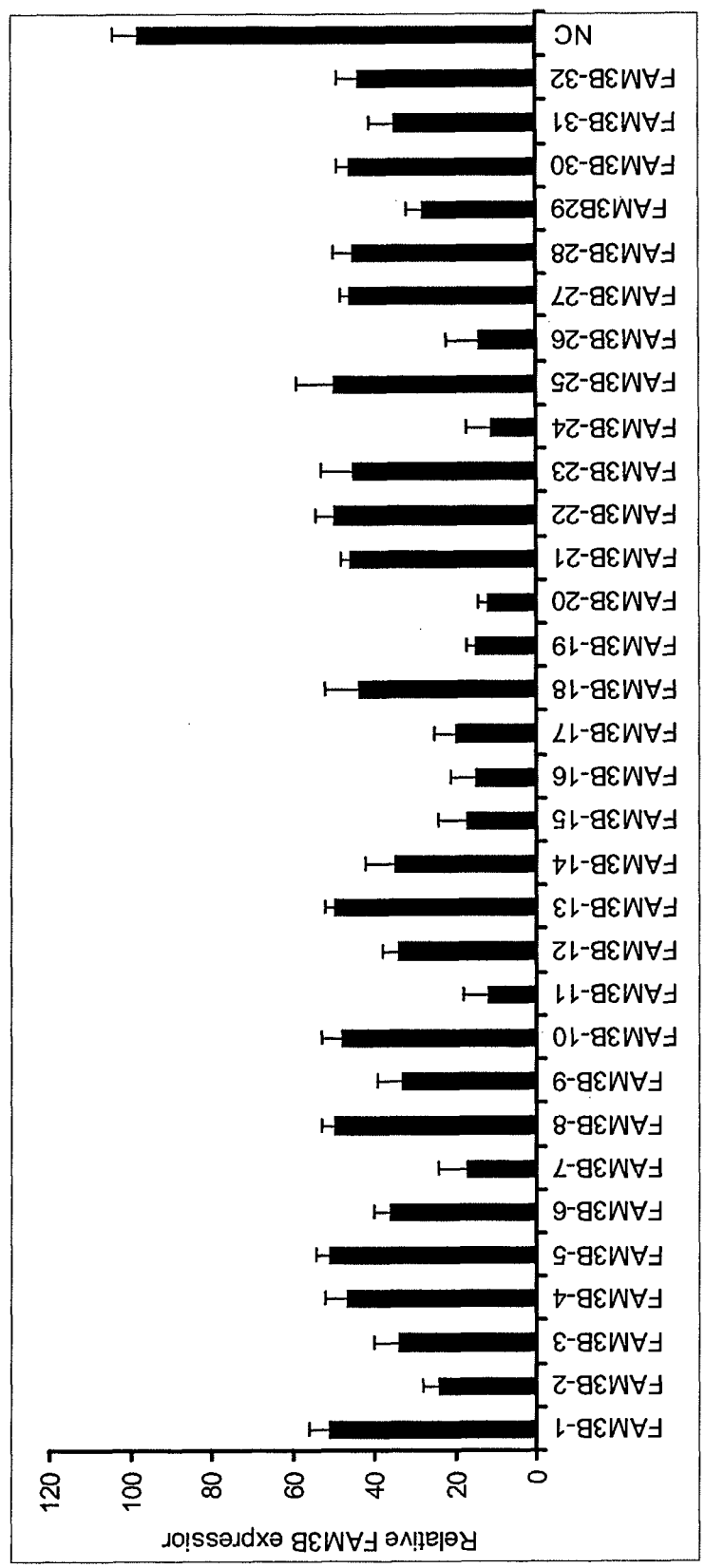

FIG. 4 showed the detection for the in vitro inhibitory efficiency of samples of human derived FAM3B-11 to FAM3B-42 provided in the present invention on FAM3B mRNA.

Figure 5:
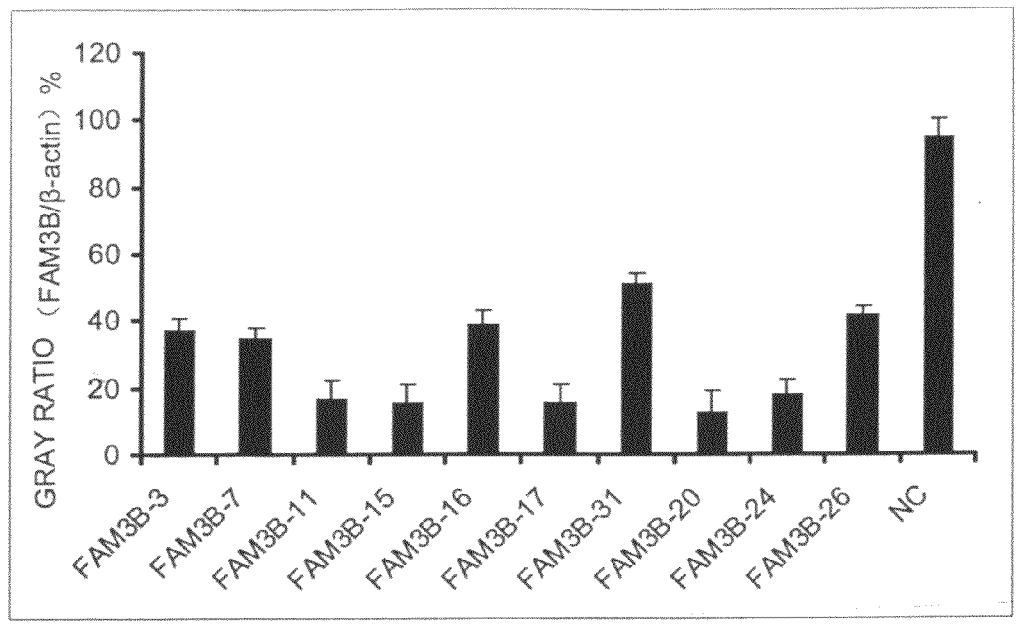

FIG. 5 showed the detection for the in vitro inhibitory effects of samples of human derived FAM3B-17, FAM3B-21, FAM3B-25, FAM3B-16, FAM3B-27, FAM3B-19, FAM3B-30, FAM3B-34 and FAM3B-36 provided in the present invention on FAM3B at the protein level.

Figure 6:
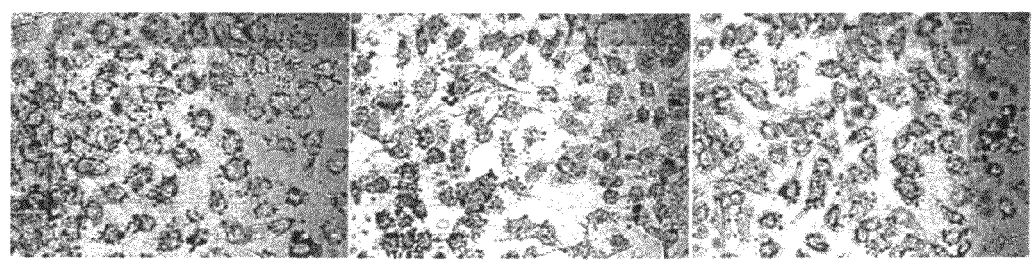

FIG. 6 showed the detection for the inhibitory effects of the sample of human derived FAM3B-30 provided in the present invention on the induced fat accumulation in HepG2 cells.

Figure 7:
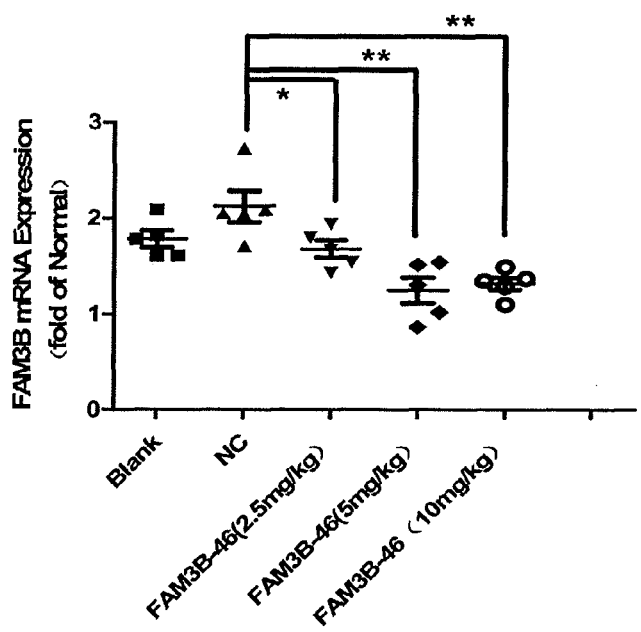

FIG. 7 showed the inhibitory effects of sample of FAM3B-46 provided in the present invention on FAM3B mRNA expression in the intestine of mice after intravenous administration.

Figure 8:
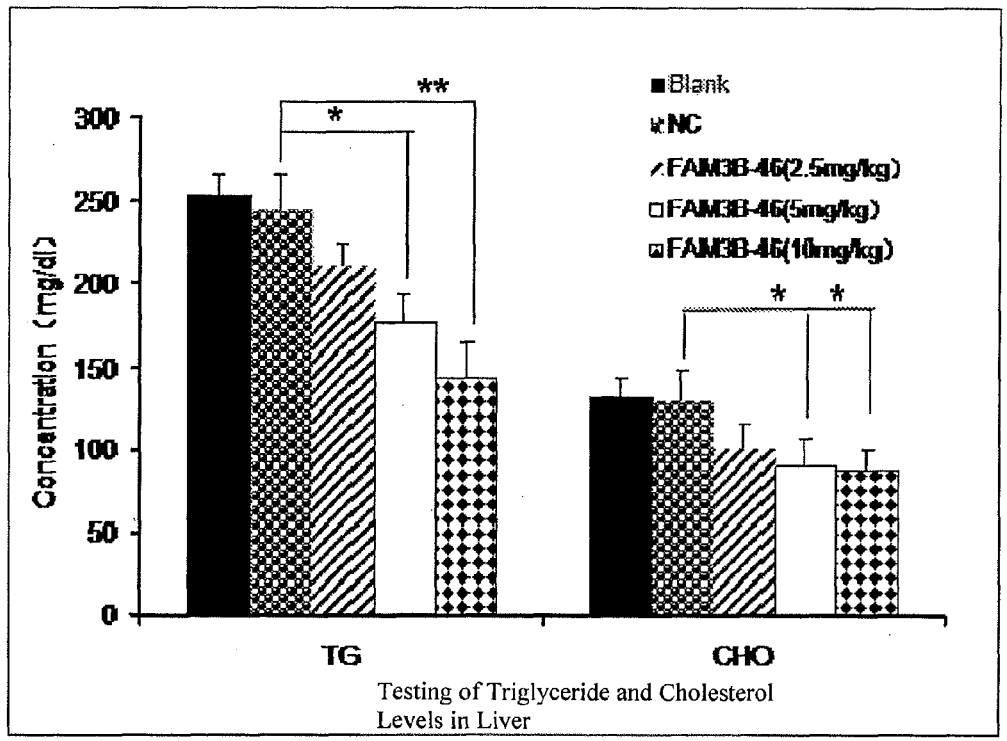

FIG. 8 showed the detection for triglyceride and cholesterol levels in hepatic tissues of the mice after they are intravenously administered with samples of FAM3B-46 provided in the present invention in different dosages.

Figure 9:
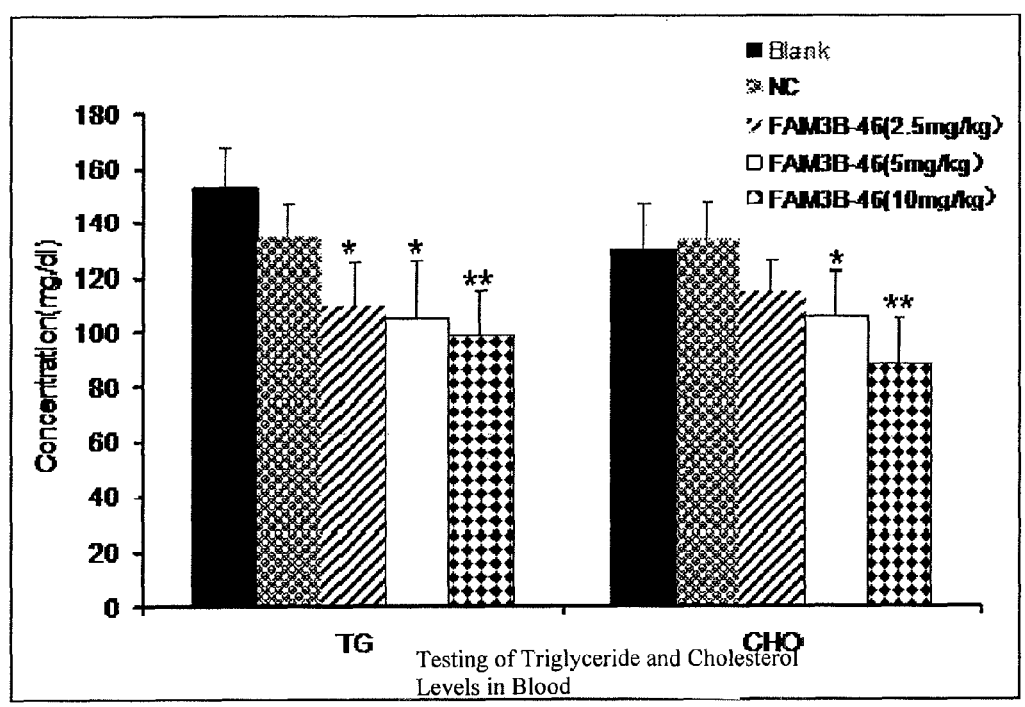

FIG. 9 showed the detection for triglyceride and cholesterol levels in blood of the mice after they are intravenously administered with FAM3B-46 provided in the present invention in different dosages.

EMBODIMENTS

The inventors carried out comprehensive studies on FAM3B gene and they found that the product of FAM3B gene may be involved in the diseases mediated by FAM3B gene expression; and they carried out studies on the sequence of FAM3B gene and found that the identity between the nucleotide sequence of FAM3B gene and the nucleotide sequence shown as SEQ ID No 1 is 90% or more. Based on the above results, the present invention provided a inhibitor, wherein the inhibitor is capable of inhibiting FAM3B gene expression to reduce the level of FAM3B gene expression product, or the inhibitor is capable of binding to the expression product of FAM3B gene to reduce the activity of promoting lipid production of FAM3B gene product.

In the present invention, there is no special limitation on the type of the inhibitors capable of inhibiting FAM3B gene expression or binding to the expression product of FAM3B gene in the present invention, as long as it can silence FAM3B gene expression or inhibit the function of promoting lipid production of FAM3B gene. For example, the examples for the inhibitor included but not limited to: small interfering nucleotides, antisense oligonucleotides, antibodies, active organic compounds and other inhibitors capable of inhibiting FAM3B gene expression or binding to the expression product of FAM3B gene.

According to an aspect of the present invention, the said inhibitor may be one or more antisense oligonucleotide that is single-strand DNA molecule with length of 14-30 bp, and the said antisense oligonucleotide has identity of 90% or more to the matched nucleotide sequence in the nucleotide sequence of FAM3B gene.

According to another aspect of the present invention, the said inhibitor can be one or more antibody, the antibody can be monoclonal antibody or polyclonal antibody, and may be antibody derived from mice or humanized antibody. In the view of structure, it can be single-strand antibody or other antibody analogs, for example, it included but not limited to aptamer or Affibody and the like.

Accordingly, the present invention further provided the use of the said inhibitor in preparing the diagnostic reagents for diagnosing the diseases mediated by FAM3B gene expression, wherein, the said inhibitor is one or more antibody and the said antibody can be monoclonal antibody or polyclonal antibody. The said disease can be hepatic adipose infiltration or disease induced by hyperlipemia, wherein the blood fat referred to serum triglyceride and/or cholesterol.

According to another aspect of the present invention, the said inhibitor can be one or more active compounds capable of inhibiting FAM3B gene expression or binding to the expression product of FAM3B gene.

According to another aspect of the present invention, the said inhibitor can be one or more small interfering nucleotides, the small interfering nucleotide is a double-strand RNA molecule, including the sense strand and the antisense strand, and the antisense strand of the small interfering nucleotide comprised the region capable of complementing to the mRNA sequence of FAM3B gene, and the length of the region is less than 30 nucleotides.

Preferably, the region in the antisense strand of the small interfering nucleotides, which is capable of complementing to the mRNA sequence of FAM3B gene, has a length of at least 15 nucleotides. The region in the FAM3B gene, which is capable of complementing to the antisense strand of the said small interfering nucleotides, is shown as one of SEQ ID Nos: 2-33.

In a preferable embodiment of the present invention, the nucleotide sequence of the said small interfering nucleotide comprises the nucleotide sequence shown as one of FAM3B-1 to FAM3B-32, or the nucleotide sequence of the said small interfering nucleotide comprised modified products of the nucleotide sequence shown as one of FAM3B-1 to FAM3B-32, wherein

```
FAM3B-1
sense strand:
                                       (SEQ ID NO: 2)
5'-GCCUGCUCAAGGUGGUGUUdTdT-3' antisense strand:
                                       (SEQ ID NO: 45)
5'-AACACCACCUUGAGCAGGCdTdT-3';

FAM3B-2
sense strand:
                                       (SEQ ID NO: 3)
5'-UUCGUGGUCUUCGCCUCCUUGdTdT-3' antisense strand:
                                       (SEQ ID NO: 46)
5'-CAAGGAGGCGAAGACCACGAAdTdT-3';

FAM3B-3
sense strand:
                                       (SEQ ID NO: 4)
5'-CCUGCUCGCAGAGCUCAUUdTdT-3' antisense strand:
                                       (SEQ ID NO: 47)
5'-AAUGAGCUCUGCGAGCAGGdTdT-3';

FAM3B-4
sense strand:
                                       (SEQ ID NO: 5)
5'-CCAGUGCUGCCUAUAGCAUdTdT-3' antisense strand:
                                       (SEQ ID NO: 48)
5'-AUGCUAUAGGCAGCACUGGdTdT-3';

FAM3B-5
sense strand:
                                       (SEQ ID NO: 6)
5'-UGACACCUAUGCCUACAGGUUdTdT-3' antisense strand:
                                       (SEQ ID NO: 49)
5'-AACCUGUAGGCAUAGGUGUCAdTdT-3';

FAM3B-6
sense strand:
                                       (SEQ ID NO: 7)
5'-UACAGGUUACUCAGCGGAGGUdTdT-3' antisense strand:
                                       (SEQ ID NO: 50)
5'-ACCUCCGCUGAGUAACCUGUAdTdT-3';

FAM3B-7
sense strand:
                                       (SEQ ID NO: 8)
5'-AUCUGCUUUGAGGAUAACCUAdTdT-3' antisense strand:
                                       (SEQ ID NO: 51)
5'-UAGGUUAUCCUCAAAGCAGAUdTdT-3';
```

```
FAM3B-8
sense strand:
                                       (SEQ ID NO: 9)
5'-UGGGAGAACAGCUGGGAAAdTdT-3' antisense strand:
                                       (SEQ ID NO: 52)
5'-UUUCCCAGCUGUUCUCCCAdTdT-3';

FAM3B-9
sense strand:
                                       (SEQ ID NO: 10)
5'-GGAAAUGUUGCCAGAGGAAdTdT-3' antisense strand:
                                       (SEQ ID NO: 53)
5'-UUCCUCUGGCAACAUUUCCdTdT-3';

FAM3B-10
sense strand:
                                       (SEQ ID NO: 11)
5'-GCCAUUGUCAACUAUGUAAdTdT-3' antisense strand:
                                       (SEQ ID NO: 54)
5'-UUACAUAGUUGACAAUGGCdTdT-3';

FAM3B-11
sense strand:
                                       (SEQ ID NO: 12)
5'-CUCUGGACCGAUGACAAAGdTdT-3' antisense strand:
                                       (SEQ ID NO: 55)
5'-CUUUGUCAUCGGUCCAGAGdTdT-3';

FAM3B-12
sense strand:
                                       (SEQ ID NO: 13)
5'-GCUCUUCAUGGUGACCUAUdTdT-3' antisense strand:
                                       (SEQ ID NO: 56)
5'-AUAGGUCACCAUGAAGAGCdTdT-3';

FAM3B-13
sense strand:
                                       (SEQ ID NO: 14)
5'-GCACAAGACUGAAUAACGAdTdT-3' antisense strand:
                                       (SEQ ID NO: 57)
5'-UCGUUAUUCAGUCUUGUGCdTdT-3';

FAM3B-14
sense strand:
                                       (SEQ ID NO: 15)
5'-GCCAUAGAAGCACUUGGAAdTdT-3' antisense strand:
                                       (SEQ ID NO: 58)
5'-UUCCAAGUGCUUCUAUGGCdTdT-3';

FAM3B-15
sense strand:
                                       (SEQ ID NO: 16)
5'-GCACUUGGAAGUAAAGAAAdTdT-3' antisense strand:
                                       (SEQ ID NO: 59)
5'-UUUCUUUACUUCCAAGUGCdTdT-3';

FAM3B-16
sense strand:
                                       (SEQ ID NO: 17)
5'-AGUAAAGAAAUCAGGAACAdTdT-3' antisense strand:
                                       (SEQ ID NO: 60)
5'-UGUUCCUGAUUUCUUUACUdTdT-3';
```

FAM3B-17
sense strand:
(SEQ ID NO: 18)
5'-GGUCUAGCUGGGUAUUUAUdTdT-3' antisense strand:
(SEQ ID NO: 61)
5'-AUAAAUACCCAGCUAGACCdTdT-3';

FAM3B-18
sense strand:
(SEQ ID NO: 19)
5'-UCCGAAAUUCAGAGAGAAAdTdT-3' antisense strand:
(SEQ ID NO: 62)
5'-UUUCUCUCUGAAUUUCGGAdTdT-3';

FAM3B-19
sense strand:
(SEQ ID NO: 20)
5'-GAUCAACCACUCUGAUGCUdTdT-3' antisense strand:
(SEQ ID NO: 63)
5'-AGCAUCAGAGUGGUUGAUCdTdT-3';

FAM3B-20
sense strand:
(SEQ ID NO: 21)
5'-GCUAAGAACAACAGAUAUUdTdT-3' antisense strand:
(SEQ ID NO: 64)
5'-AAUAUCUGUUGUUCUUAGCdTdT-3';

FAM3B-21
sense strand:
(SEQ ID NO: 22)
5'-CUGCAGAGAUCCAGAUAGAdTdT-3' antisense strand:
(SEQ ID NO: 65)
5'-UCUAUCUGGAUCUCUGCAGdTdT-3';

FAM3B-22
sense strand:
(SEQ ID NO: 23)
5'-CCAGAUAGAAGGCUGCAUAdTdT-3' antisense strand:
(SEQ ID NO: 66)
5'-UAUGCAGCCUUCUAUCUGGdTdT-3';

FAM3B-23
sense strand:
(SEQ ID NO: 24)
5'-CUGCAUACCCAAAGAACGAdTdT-3' antisense strand:
(SEQ ID NO: 67)
5'-UCGUUCUUUGGGUAUGCAGdTdT-3';

FAM3B-24
sense strand:
(SEQ ID NO: 25)
5'-GAGUAAAUGUGUUCUGUAUdTdT-3' antisense strand:
(SEQ ID NO: 68)
5'-AUACAGAACACAUUUACUCdTdT-3';

FAM3B-25
sense strand:
(SEQ ID NO: 26)
5'-AAACAAAUGCAGCUGGAAUdTdT-3' antisense strand:
(SEQ ID NO: 69)
5'-AUUCCAGCUGCAUUUGUUUdTdT-3';

FAM3B-26
sense strand:
(SEQ ID NO: 27)
5'-GCCCAUAUUUGAUGAGUAUdTdT-3' antisense strand:
(SEQ ID NO: 70)
5'-AUACUCAUCAAAUAUGGGCdTdT-3';

FAM3B-27
sense strand:
(SEQ ID NO: 28)
5'-GUUGUAAACCAAUGAACAUdTdT-3' antisense strand:
(SEQ ID NO: 71)
5'-AUGUUCAUUGGUUUACAACdTdT-3';

FAM3B-28
sense strand:
(SEQ ID NO: 29)
5'-GUAGUGAAGAUGUCAAUUAdTdT-3' antisense strand:
(SEQ ID NO: 72)
5'-UAAUUGACAUCUUCACUACdTdT-3';

FAM3B-29
sense strand:
(SEQ ID NO: 30)
5'-GAUGUCAAUUAGCAGGAAAdTdT-3' antisense strand:
(SEQ ID NO: 73)
5'-UUUCCUGCUAAUUGACAUCdTdT-3';

FAM3B-30
sense strand:
(SEQ ID NO: 31)
5'-GCAGGAAACUAAAAUGAAUdTdT-3' antisense strand:
(SEQ ID NO: 74)
5'-AUUCAUUUUAGUUUCCUGCdTdT-3';

FAM3B-31
sense strand:
(SEQ ID NO: 32)
5'-GAAAGAGGGUUGGGAGAAAdTdT-3' antisense strand:
(SEQ ID NO: 75)
5'-UUUCUCCCAACCCUCUUUCdTdT-3';

FAM3B-32
sense strand:
(SEQ ID NO: 33)
5'-AGACAGCCCUGCAGAGAGAdTdT-3' antisense strand:
(SEQ ID NO: 76)
5'-UCUCUCUGCAGGGCUGUCUdTdT-3'.

Preferably, the nucleotide sequence of the said small interfering nucleotide is the nucleotide sequence shown as FAM3B-3, FAM3B-7, FAM3B-11, FAM3B-15, FAM3B-16, FAM3B-17, FAM3B-20, FAM3B-24, FAM3B-26 or FAM3B-31.

Preferably, the nucleotide sequence of the said small interfering nucleotide is the nucleotide sequence shown as FAM3B-11, FAM3B-15, FAM3B-17, FAM3B-20 and FAM3B-24.

According to the present invention, the said modification is at least one of the modifications as below:
(1) Modifications on the phosphodiester bond moiety linking nucleotide in the nucleotide sequence;
(2) Modifications on 2'-OH of ribose moiety in the nucleotide sequence;
(3) Modifications on basic groups in the nucleotide sequence.

The said chemical modification is well known to those skilled in the art, the said modifications on phosphodiester bond moiety referred to the substitutions on oxygen in the phosphodiester bond, including sulfur substitution in phosphoric acid moiety, shown as formula 1; and borane substitution in phosphoric acid moiety, shown as formula 2. These two modifications can stabilize the structure of nucleotide and maintain high specificity and affinity of base group matching.

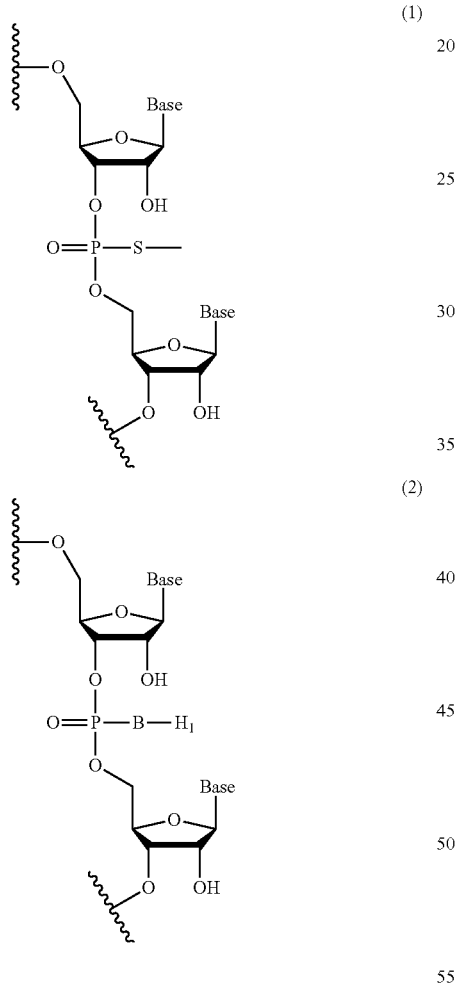

The said modifications on ribose moiety referred to the modifications on 2'-OH in pentaglucose moiety of the nucleotides, in other words, some substituent groups are introduced into the —OH position in the ribose moiety, such as modification as 2'-fluor(o) substitution, shown as formula 3; modification as 2'-oxo-methyl substitution, shown as formula 4; modification as 2'-oxo-ethidene-methoxyl substitution, shown as formula 5; modification as 2,4'-dinitrophenol substitution, shown as formula 6; modification as locked nucleic acid (LNA), shown as formula 7; modification as 2'-amio substitution, shown as formula 8; 2'-deoxy-modification, shown as formula 9.

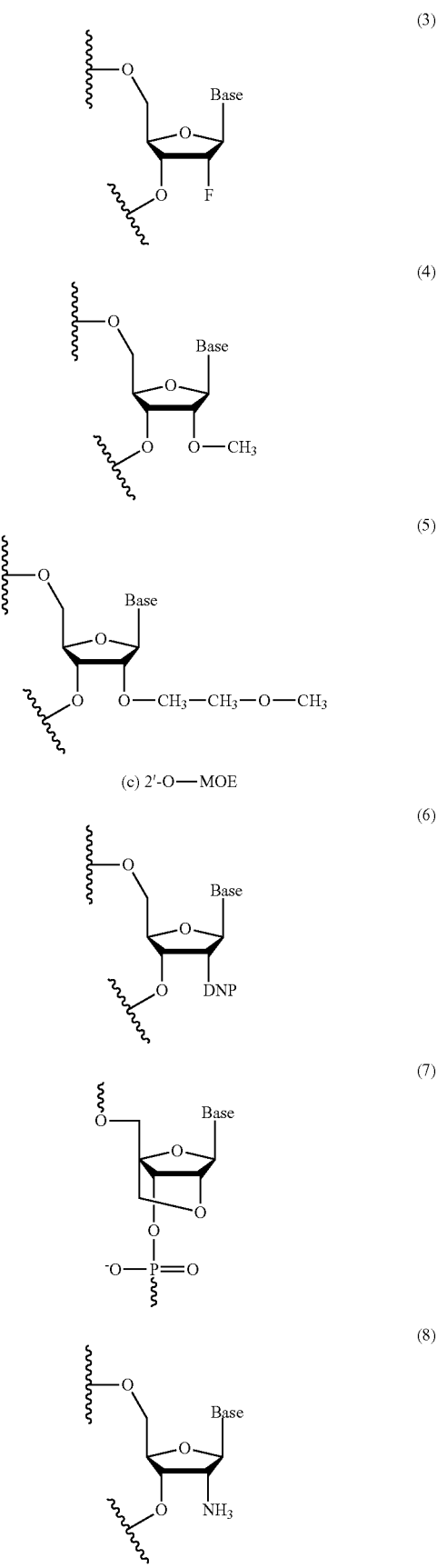

(9)

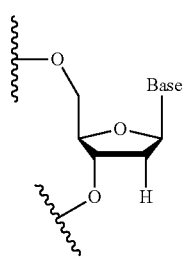

The said modifications on basic groups referred to the modifications on basic groups of nucleotides, such as modification into 5'-bromouracil, shown as formula 10; modification into 5'-iodouracil, shown as formula 11; modification into N-methyl-uracil, shown as formula 12; modification into 2,6-diaminopurine, shown as formula 13.

(10)

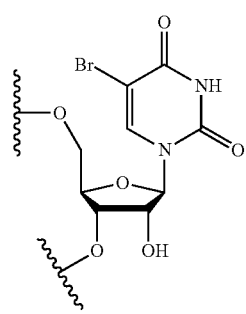

(11)

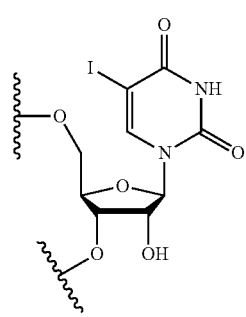

(12)

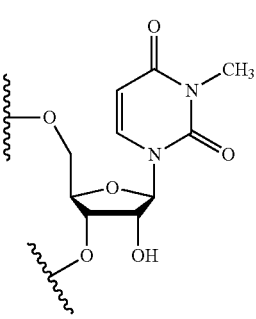

(13)

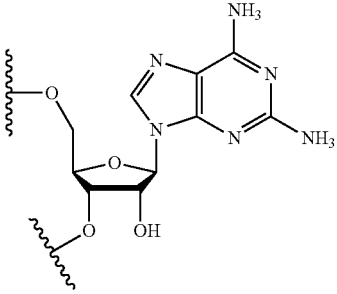

Preferably, the said modification reinforced the capability of the modified small interfering nucleotide in resisting the hydrolysis by nucleases in the cells.

Furthermore, in order to facilitate the small interfering nucleotide to enter the cells, cholesterol and other lipophilic groups can be introduced into the terminal of the sense strand in the small interfering nucleotide on the basis of modifications as mentioned above, and the lipophilic groups comprises the groups binding to small interfering nucleotide by covalent bond, such as cholesterol, lipoproteins, vitamin E and others introduced at the end, in order to facilitate to pass through the cell membrane comprised of lipid bilayer and interact with mRNA in the cells.

Therefore, cholesterol is connected at the terminal of sense strand of the small interfering nucleotide under an optimal implementation way.

At one strand from the sense strand and the antisense strand of the small interfering nucleotide is connected to the ligand under the other optimal implementation way.

At the same time, the small interfering nucleotide can also be subjected to modifications with noncovalent bond, for example, binding to phospholipid molecules, polypeptides, cationic polymers and others via hydrophobic bond or ionic bond to increase stability and biological activities.

The methods for preparing small interfering nucleotide provided by the present invention included the design of small interfering nucleotide sequence and the preparation of small interfering nucleotides.

The said design of small interfering nucleotide referred to the utilization of the cDNA sequence of FAM3B gene (SEQ ID NO. 1) (the accession number in Genebank is NM_058186) as the template, and the selection of the nucleotide sequence of 15-27 bp in the conservative region of FAM3B to design corresponding small interfering nucleotides.

The said design of the small interfering nucleotide for FAM3B gene is carried out according to the principle as below:

Nucleotide sequence of 15-27 bp is selected from 1-1384 bp in the cDNA sequence of FAM3B gene. The selection of the nucleotide sequence of 15-27 bp is carried out with reference to the principle as below: (1) GC content between 35-60%, (2) avoidance of locating in the region of repeated sequence or low-complexity sequence, (3) avoidance of existing of continuous base sequence longer than 4 nucleotides, (4) avoidance of comprising single nucleotide polymorphism site, (5) avoidance of locating in the region of 50-100 bp around the initiation codon or the stop codon in the open reading frame, besides, composition and thermodynamic properties of the nucleotide sequence should also be analyzed. The target of the small interfering nucleotide candidates is subjected to homology alignment with gene sequence of human by BLAST, the sequence with high sequence homology to other gene is excluded (more than 14 bases) in order to make sure that the target of the small interfering nucleotide did not inhibit other unrelated genes, but showed specific inhibitions on FAM3B gene.

Finally, two deoxythymidines are added at the 3' end of the obtained nucleotide sequence of 15-27 bp and used as the sense strand of the small interfering nucleotide, and two deoxythymidines are added at the 3' end of the complementary sequence of the nucleotide sequence of 15-27 bp and used as the antisense strand of the small interfering nucleotide.

According to the present invention, the said method for preparing small interfering nucleotide is well known for the skilled in the art, for example, the said small interfering nucleotide can be obtained by chemical synthesis, or obtained by expression using plasmids and/or viral vectors.

The synthesis of the sequence of the said small interfering nucleotide can be carried out by chemical synthesis, or synthesized by customizing from the biological technological company engaged in nucleotide synthesis, for example, synthesis by Shanghai GenePharma Company.

Generally, the said chemical synthesis method included four procedures as followed: (1) synthesis of oligoribonucleotide; (2) deprotection; (3) purification and isolation; (4) desalination.

For example, the procedures for chemical synthesis of small interfering nucleotide for the nucleotide sequence shown as FAM3B-1 are as followed:

(1) Synthesis of oligoribonucleotide: Synthesis of oligoribonucleotide is carried out on an automated DNA/RNA synthesizer (for example, Applied Biosystems EXPEDITE8909), and the nucleotide is connected one by one according to the sequence of the nucleotide shown in FAM3B-1. Since small interfering nucleotide is composed of 15-27 oligoribonucleotides and 2 deoxythymidylates. Therefore, the starting material is 5'-O-para-dimethoxyl-thymine deoxyriboside linked to solid-phase, and each cycled synthesis can be divided into four steps, i.e., the first step is the elution of the protecting group on 5' position on the thymine deoxyriboside at the presence of trichloroacetic acid; the second step is the coupling of 5'-O-para-dimethoxyl-trityl-thymine deoxyriboside phosphoramidite to the former thymine deoxyriboside after de-protection at the presence of the active catalyst S-ethyltetrazole to produce di-thymine deoxyriboside phosphite trimester, duration and frequency of coupling are all implemented according to the procedures provided by the manufacturer; the third step is to oxidize the coupled deoxyriboside phosphite trimester into di-thymine deoxyriboside phosphotriester at the presence of 0.05 M iodine solution; the fourth step is acetylation, small amount of unreactive active groups on the solid phase (such as amid and hydroxyl) are transformed into esters or amides at the presence of acetic anhydride, thus the purpose of blocking is achieved in order to reduce the general production of side products, and this cycle is repeated until the synthesis of entire nucleotide sequence is finished.

(2) De-Protection

The synthetic solid-phase small interfering nucleotide is transferred into a small bottle that can be tightly sealed, 1 ml of mixture of ethanol and amine is added (the volume ration is 1:3), then the bottle is tightly sealed and incubated in an incubator at 55-70° C. for 2-30 hours, the solution is removed and the solid phase is eluted with double-distilled water and the eluant is collected and then dried to remove the solvent. Afterwards, 1 ml of tetra-butyl ammonium fluoride in tetrahydrofuran solution (1 M) is added and the mixture is kept at room temperature for 4-12 hours, and the crude product of small interfering nucleotide can be obtained after ethanol precipitation.

(3) Purification and Isolation

The crude product of small interfering nucleotide is dissolved in 2 ml ammonium acetate solution and separated by using C18 high pressure liquid chromatography, and the major products of small interfering nucleotide are collected (eluant A: 0.1 M ammonium acetate; eluant B: 20% by weight of 0.1 M ammonium acetate and 80% by weight of acetonitrile) by using gradient elution according to the standard procedures for C18 high pressure liquid chromatography, the solvent in the major products is removed and 5 ml of 80% by weight of acetic acid solution is added; the mixture is kept at room temperature for 15 minutes, afterwards, this solution is subjected to anion exchange separation according to the standard procedures for DEAE-5PW exchange column (DEAE-5PW, anion exchange column), finally the small interfering nucleotide with a purity higher than 90% by weight can be obtained (gradient elution: eluant A: 0.025 M Tris-HCl, 0.025 M NaCl, pH=8, 5% by weight of acetonitrile; eluant B: 0.025 M Tris-HCl, 2.0 M NaCl, pH=8, 5% by weight of acetonitrile).

(4) Desalination

The salts in the purified small interfering nucleotide are removed by dialysis, then the solution of small interfering nucleotide is subjected to filtration sterilization and exsiccation. Subsequently the oligo-ribonucleic acids of sense strand and antisense strand are subjected to annealing to product stable double-strand small interfering nucleotides, the method is as followed: the oligo-ribonucleic acids of sense strand and antisense strand are mixed and dissolved in 1-2 ml buffer (10 mM Tris, pH=7.5-8.0, 50 mM NaCl), the solution is heated to 95° C. and slowly cooled to room temperature, finally this solution is stored in a refrigerator at 4° C. for further use at any time.

Besides chemical synthesis, small interfering nucleotide can also be obtained by expression using plasmids and/or viral vectors, and shRNA with hairpin structure is obtained, and they are composed of 50-90 nucleotides. The structure of shRNA is as followed:

Enzymatic sites are located at both ends (such as BamHI and EcoRI) and a loop sequence can be found in the middle (such as GAAGCTTG), and it is inserted into the vector digested with corresponding restriction enzymes by cloning techniques, and the small interfering nucleotide can be stably expressed after it is integrated into the chromosome, For example, 5'-GATCCG- sense strand GAAGCTTG-antisense strand TTTTTTGGAATT-3'-(SEQ ID NO: 77).

The present invention also provided a cell, wherein the cell comprised the inhibitor provided in the present invention. The said cells can be common mammalian cells, such as human cells.

The present invention also provided a vector, wherein the vector comprised the inhibitor provided in the present invention.

The present invention also provided a inhibitor composition, wherein the inhibitor composition comprised the inhibitor provided in the present invention as the active ingredient.

Preferably, the said inhibitor composition may further comprise carrier, there is no specific limitation on the dosage of the carrier, for example, for 100 part by weight of the said inhibitor, and the content of the said carrier can be 100-10000000 part by weight. The category of the said carrier can be selected within a very wide range, for example, it can be one or more selected from liposome, nanoparticle, polypeptide complex, protein complex, lipid complex, cation polymer, polymers with tree-like structure, and other high polymers and macromolecule materials.

According to an aspect of the present invention, the said pharmaceutical combination can be a injection.

In the present invention, the said injection may further comprise pharmacologically acceptable adjuvant, and the dosage of the pharmacologically acceptable adjuvant can be selected within a wide range, preferably, for 100 part by weight of inhibitor, the content of the said pharmacologically acceptable adjuvant can be 100-10000000 part by weight.

In the present invention, there is no special limitation on the said pharmacologically acceptable adjuvant, for example, it can be phosphoric acid buffer with pH value of 4.0-9.0, Tris HCl buffer with pH value of 7.5-8.5, physiological saline, or phosphate salt buffer with pH value of 5.5-8.5, preferably, the said pharmacologically acceptable adjuvant is phosphate buffer with pH value of 4.0-9.0.

According to the present invention, the said injection may further comprise protective additive and/or osmotic regulator; the content of the said protective additive is 0.01-30% by weight of the injection, and the said protective additive can be one or more of inositol, sorbitol and sucrose; the content of the said osmotic regulator is capable of making the osmotic pressure of the said injection to be 200-700 milliosmole/kilogram, and the said osmotic regulator is sodium chloride and/or potassium chloride.

When the said pharmaceutical combination in the present invention is injected, the dosage can be the common dosage in this field, for example, a single injection for 1-1000 mg/kg body weight; for specific uses, the said dosage can be determined by physicians according to various parameters, particularly age and body weight of the patients for treatments as well as the severity degree of the diseases.

The present invention also provided a method for inhibiting the expression of FAM3B gene or for inhibiting the activity of promoting lipid production of FAM3B gene product, wherein, the method comprised using the inhibitor or the inhibitor composition provided in the present invention to reduce the level of FAM3B gene expression; or to reduce the activity of promoting lipid production of FAM3B gene product.

The present invention also provided a method for preventing and/or treating the disease mediated by FAM3B gene expression, wherein, the method comprises inhibiting FAM3B gene expression in patients to reduce the level of FAM3B gene expression product; or reducing the activity of promoting lipid production of FAM3B gene product. There is no limitation on the method of inhibiting FAM3B gene expression in the patients to reduce the expression level of FAM3B gene; or reducing the activity of promoting lipid production of FAM3B gene product, and the skilled in the art can properly select it after understanding the contents in the present invention, for example, the method may comprise administering the inhibitor or the inhibitor composition provided in the present invention to the patients.

In a preferable embodiment, the said disease mediated by FAM3B gene expression is hepatic adipose infiltration.

In another preferable embodiment, the said disease mediated by FAM3B gene expression is the disease induced by hyperlipemia, wherein, the said blood fat referred to serum triglyceride and/or cholesterol.

The present invention also provided the uses for the said inhibitor in preparing the pharmaceuticals for preventing and/or treating the disease mediated by FAM3B gene expression. Preferably, the said disease mediated by FAM3B gene expression is hepatic adipose infiltration or the diseases induced by hyperlipemia, wherein the said blood fat referred to serum triglyceride and/or cholesterol.

The present invention is further illustrated by combining the examples as below, and the reagents and the culture media in the present invention are all commercially available unless otherwise indicated.

Example 1

Design and Synthesis of Small Interfering Nucleotide of Human Derived FAM3B Gene The nucleotide sequences of 19-21 bp are selected from cDNA sequence of human derived FAM3B gene in the range of 1-1384 bp, whose sequence is relatively conservative (the accession number in Genbank is NM_058186) (SEQ ID NO. 1). Two deoxythymidine nucleotides are added in the 3' end of the obtained nucleotide sequences of 19-21 bp, which is used as the sense strand of the small interfering nucleotide, and two deoxythymidine nucleotides are added in the 3' end of the complementary sequence of the nucleotide sequences of 19-21 bp, which is used as the antisense strand of the small interfering nucleotide. The nucleotide sequences are shown in Table 1.

The selection of the nucleotide sequences of 19-21 bp is based on the principles as below:

(1) GC content between 35-60%;
(2) avoidance of locating in the region of repeated sequences or low-complexity sequences;
(3) avoidance of existing of continuous base sequences longer than 4 nucleotides;
(4) avoidance of comprising single nucleotide polymorphism site;
(5) avoidance of locating in the region of 50-100 bp around the initiation codon or the stop codon in the open reading frame.

Besides, composition and thermodynamic properties of the nucleotide sequences should also be analyzed. The target of the small interfering nucleotide candidates is subjected to homology alignment with gene sequences of human by BLAST, the sequences with high sequence homology to other genes are excluded (more than 14 bases) in order to make sure that the small interfering nucleotides did not inhibit other unrelated genes.

The designed small interfering nucleotide is chemically synthesized by Shanghai GenePharma Company.

Example 2

Design and Synthesis of Small Interfering Nucleotide of Mouse Derived FAM3B Gene In order to carry out the animal test, the nucleotide sequences of 19-21 bp are selected from cDNA sequence of mouse derived FAM3B gene in the range of 1-871 bp, whose sequence is relatively conservative (the accession number in Genbank is NM_020622) (SEQ ID NO. 44). The design of siRNA is carried out according to the principles in example 1 and the nucleotide sequence is shown in Table 2.

The designed small interfering nucleotide is chemically synthesized by Shanghai GenePharma Company.

Example 3

Chemical Modification of Small Interfering Nucleotide

In order to reinforce the stability of small interfering nucleotide and improve the hepatic targeting of pharmaceutical administration, chemical modification design is carried out for the small interfering nucleotide of mouse derived FAM3B gene and the principles for design are as followed: modification as 2'-oxo-methyl substitution is carried out on 2'-OH in the pentose of U, C and G in the sense strand of the small interfering nucleotide, and cholesterol is connected at the terminal; modification as 2'-fluor(o) substitution is carried out on the 2'-OH in the pentose of U and C in the antisense strand of the small interfering nucleotide. The small interfering nucleotides with chemical modification are synthesized by Shanghai GenePharma Company. The information for the sequences of the modified small interfering nucleotides FAM3B-43 to FAM3B-46 are shown in Table 3.

Example 4

Determination of the Activity of Small Interfering Nucleotides of Mouse Derived FAM3B Gene at Cellular Level (1) Construction of the Plasmid Comprising the Target of Small Interfering Nucleotide The DNA Oligo at corresponding target in the small interfering nucleotide is ligated into the highly efficient expression vector siQuant comprising double fluorescence reporter genes, and the plasmid is used to transform the Top 10 competent cells, and finally the plasmid is extracted by using the plasmid extraction kit according to the instructions from Promega.

(2) HEK293a Cell Culture

The cells are incubated in the DMEM culture solution comprising 10% fetal bovine serum, 2 mM L-glutamine, 100 µ/ml penicilin and 100 µg/ml streptomycin at 37° C. and 5% $CO_2$, and the cells are sub-cultured for every 48 hours and fresh culture medium is used.

(3) Transfection of HEK293a Cells

Transfection is carried out according to the instructions for Lipofectamine™ 2000 liposome (Invitrogen), the control plasmid, the plasmid comprising the target site of the small interfering nucleotide and corresponding small interfering nucleotide (FAM3B-33 to FAM3B-42) are co-transfected respectively, and the final concentration of the small interfering nucleotide is 10 nM. The unrelated small interfering nucleotide is used as the negative control: (sense strand: 5-UUCUCCGAACGUGUCACGUTT-3 (SEQ ID NO: 78); antisense strand: 5-ACGUGACACGUUCGGAGAATT-3 (SEQ ID NO: 79)), the culture medium is discarded 24 hours after transfection, and the cells are collected and subjected to double luciferase activity determination.

(4) Determination of the Activity

The cells are rinsed with PBS for three times and 5 minutes each; the cell lysis buffer is then added and the luciferase catalysis substrate is added for coloration for 10 minutes after complete lysis, subsequently the stop solution is added to determine the intensity of fluorescence signals, and the inhibition ratio of the small interfering nucleotides are calculated. The results are shown in FIG. 1.

It can be found from FIG. 1 that the small interfering nucleotides provided in the present invention FAM3B-33 to FAM3B-42 can efficiently inhibit the activity of the target of FAM3B, particularly that the inhibitory activities of the small interfering nucleotides FAM3B-34, FAM3B-35, FAM3B-38, FAM3B-39, FAM3B-40, FAM3B-41 and FAM3B-42 on FAM3B genes are as high as 80-97% respectively, indicating that the small interfering nucleotides provided in the present invention has excellent inhibitory activities on the target in FAM3B gene.

Example 5

Treatments on Hepatic Adipose Infiltration in Animals by Using Small Interfering Nucleotides (1) Induction on hepatic adipose infiltration model in mice. 10 male C57BL/6J mice (purchased from the department of experimental animals, Medical Division of Peking University) with age of 8-10 weeks are divided into two groups (normal diet and MCD diet). MCD (high-fat, methionine-choline deficient) diet is a common program for the investigations on non-alcoholic fatty liver in this field. The hepatic adipose infiltration model in mice is obtained after treatments for 10-16 weeks.

(2) Treatments on Hepatic Adipose Infiltration Using Small Interfering Nucleotides 1.2 mg (0.09 µmol) small interfering nucleotides from FAM3B-43 to FAM3B-46 with modification in the example 3 is dissolved in 1.5 ml RNAase free sterilized physiological saline to prepare a solution comprising 60 µmol/L small interfering nucleotides, and it is mixed in certain proportion with the carrier material. The injection is obtained after the mixed small interfering nucleotide is added into 5 ml RNAase free sterile physiological saline (the concentration of the small interfering nucleotide is 0.25 mg/ml). The hepatic adipose infiltration model mice are subjected to conventional tail intravenous injection with the prepared injections from step (1) respectively, and the dosage for injection is 10 ml injection/kg body weight, while the mice in the blank control group are injected with physiological saline in the same volume once for every three days.

(3) Determination of the Efficacy for the Treatment on Hepatic Adipose Infiltration by Using Small Interfering Nucleotides The animals are killed 15 days after the treatments and the sections from their hepatic tissues are used for detecting lipid accumulation (oil red O staining and HE staining after paraffin sectioning), the results are shown in FIG. 2; the results showed that the small interfering nucleotide FAM3B-46 can effectively reduce the degree of hepatic adipose infiltration in the mice, and it showed significant dose-dependent manner at 2.5 mg/kg, 5 mg/kg and 10 mg/kg.

RNA samples are extracted from the hepatic tissues and real-time PCR is carried out to determine the inhibitory rates of the small interfering nucleotides from FAM3B-43 to FAM3B-46 on FAM3B mRNA in the hepatic tissues, and the results are shown in FIG. 3. The small interfering nucleotides provided in the present invention from FAM3B-43 to FAM3B-46 can significantly reduce the expression of FAM3B in hepatic tissues; particularly, the inhibitory rates of the small interfering nucleotides FAM3B-45 and FAM3B-46 on the expression of hepatic FAM3B gene are both higher than 60%.

It can be found from the experiments as above that the inhibitor provided in the present invention can significantly inhibit lipid accumulation in hepatic cells by inhibiting FAM3B gene expression or inhibiting the activity of FAM3B gene product, thus it can be used for preventing and/or treating hepatic adipose infiltration.

Example 6

Inhibition on FAM3B Gene Expression in HepG2 Cells by Using Small Interfering Nucleotides (1) HepG2 Cell Culture HepG2 cells (purchased from ATCC) are inoculated and cultured in the 24-well culture plate in a density of $1\times10^5$ cells/well with the complete DMEM culture medium comprising 10% fetal bovine serum, 2 mM L-glutamine and 380 μg/ml G418, and the cells are incubated at 37° C. in an incubator with 5% $CO_2$. The cells are sub-cultured for every 72 hours and fresh culture medium is used.

(2) Transfection with Small Interfering Nucleotides

The cells are digested with 0.25% trypsin 24 hours before the transfection, then the cells are counted and inoculated into the 24 well plate in a density of $1\times10^5$ cells/ml, and 1000 μl cells are added in each well. Lipofectamine™ 2000 liposome from Invitrogen Company is used for the transfection with the small interfering nucleotides obtained from example 1 (FAM3B-1 to FAM3B-32) respectively, and unrelated small interfering nucleotide (the sense strand: 5-UUCUC-CGAACGUGUCACGUTT-3 (SEQ ID NO: 78); the antisense strand: 5-ACGUGACACGUUC GGAGAATT-3 (SEQ ID NO: 79)) is used as the negative control.

(3) Inhibitory Effects of the Small Interfering Nucleotides on mRNA Expression of FAM3B Gene The cells are collected 24 hours after the transfection and total RNA is extracted according to the instructions from Promega. Real-time PCR is used to determine the mRNA expression level of FAM3B gene in the HepG2 cells trasfected with the small interfering nucleotides from FAM3B-1 to FAM3B-32. The primers for FAM3B are as followed: the upstream primer: 5'-aatccctgctcttcatggtg-3', the downstream primer: 5'-gagttccaagccttttgctg-3'; (3-actin is used as the internal reference gene, and the primers are as followed: the upstream primer: 5'-ctgggacgacatggagaaaa-3', the downstream primer: 5'-aaggaaggctggaagagtgc-3'. The inhibitory activities of the small interfering nucleotides are calculated according to the formula as below, and the results are shown in FIG. 4.

The inhibitory activity of the small interfering nucleotide= [1-(copy number of FAM3B gene after transfection with the small interfering nucleotide/copy number of (3-actin after transfection with the small interfering nucleotide)/(copy number of FAM3B gene in the control well/copy number of β-actin in the control well)]×100%.

It can be found from FIG. 4 that the small interfering nucleotides provided in the present invention (from FAM3B-1 to FAM3B-32) can significantly inhibit the expression of FAM3B gene in HepG2 cells, particularly that the inhibitory rates of the small interfering nucleotides FAM3B-20, FAM3B-11, FAM3B-24, FAM3B-15 and FAM3B-17 on FAM3B mRNA in HepG2 cells are higher than 80%, indicating that the small interfering nucleotides provided in the present invention can significantly inhibit the expression of FAM3B gene in HepG2 cells.

(4) Inhibition on FAM3B Protein Expression by Using Small Interfering Nucleotides After the cells transfected according to step (2) in example 6 are cultured for 48 hours, the cells are disrupted by using the protein lysis buffer and the total proteins are extracted, and the protein sample is examined according to the standard procedure for Western blot. For the detection of FAM3B protein, the membrane is incubated with the rabbit derived anti-FAM3B antibody (R&D systems), the secondary antibody is the peroxidase labelled horse anti-rabbit antibody (Zhongshan Jinqiao); the antibody for detecting the internal reference β-actin: the primary antibody is mouse derived anti-β-actin antibody, and the secondary antibody is the peroxidase labelled goat anti-mouse antibody, and the results are subjected to grayscale comparison shown as FIG. 5. It can be found from FIG. 5 that the small interfering nucleotides in the present invention FAM3B-20, FAM3B-11, FAM3B-24, FAM3B-15 and FAM3B-17 can significantly inhibit FAM3B protein expression in HepG2 cells.

Example 7

Inhibition on Lipid Accumulation in HepG2 Cells by Using Small Interfering Nucleotides (1) Induction of Lipid Accumulation in HepG2 Cells The cells are inoculated in the 24 well culture plate in a density of $2\times10^4$ cells/1 mL, 20% fat emulsion for medical use is added in each well in a dosage of 2 ml/L, and the cells are cultured for 48 hours. The culture is stopped and oil red O staining is carried out to observe the lipids in the cells. The operations are as followed: the cells are rinsed with PBS for three times and 5 minutes each; then the cells are fixed with 50% isopropanol for 1 min and stained with oil red O for 10 min; the cells are rinsed with distilled water for three times and 1 min each; the cells are observed and photographed under a microscope. Normally, the cells might be not stained or only slightly stained, large amount of lipids accumulated in the cells after induction with fat emulsion for medical use, and red lipid droplets can be detected under the microscope after the staining with oil red O.

(2) Determination of the Inhibitory Effects on Lipid Accumulation in HepG2 Cells The inhibitory effects of the small interfering nucleotide FAM3B-20 on lipid accumulation in the cells are examined, and the procedures are as followed: the cells are inoculated in the cell culture plate in a density of $1\times10^4$ cells/1 mL, after the cells are induced with 20% fat emulsion for medical use for 48 hours, the small interfering nucleotide and Lipofectamine™ 2000 liposome (Invitrogen) are added in each well for transfection, and the final concentration of the small interfering nucleotide is 50 nM. Unrelated small interfering nucleotides (the sense strand: 5-UUCUCCGAAC GUGU-CACGUTT-3 (SEQ ID NO: 78); the antisense strand: 5-ACGUGACACGUUCGGAGAATT-3 (SEQ ID NO: 79)) are used as the negative control. The culture medium is discarded 48 hours after the transfection, and oil red O staining is carried out. The operations are carried out according to step (1). Grayscale analysis is carried out by using the color image analytical system on a computer (small grayscale value and dark staining with oil red indicated large area of fatty deposition and high intensity), and the results are shown in FIG. 6.

It can be found from FIG. 6 that the small interfering nucleotide FAM3B-20 in the present invention can significantly inhibit fatty deposition in hepatic cells.

It can be found from the experiments as mentioned above that the inhibitor in the present invention can significantly inhibit lipid accumulation in hepatic cells by inhibiting FAM3B gene expression or inhibiting the activity of FAM3B gene product, thus it can be used for preventing and/or treating hepatic adipose infiltration.

Example 8

Efficacy of Small Interfering Nucleotides in Treating Hepatic Adipose Infiltration Specially modified small interfering nucleotides are used for the tests for treating hepatic adipose infiltration on human body after certain processing for preparations. The subjects are all moderate or serious patients of hepatic adipose infiltration, and strict evaluations are carried out for pathogenetic conditions and physiological status of the patients before pharmaceutical administration. Intravenous administration in a dosage of 1 mg/kg body weight/3 days is carried out for some time, and changes in pathogenetic conditions and physiological status of the patients are compared before and after the treatments at 15, 30 and 60 days, and evaluations are carried out on the efficacy of the small interfering nucleotides in the present invention in treating hepatic adipose infiltration.

Example 9

Efficacy of Anti-FAM3B Antibody in Treating Hepatic Adipose Infiltration

We produced anti-FAM3B polyclonal antibody by expressing and purifying FAM3B protein and immunize mice. The valency of the antibody is 1:10000. After purification with protein A column, the IgG component is obtained and used for the injection on the mice. The dosage is controlled between 0.1 μg to 10 mg for every kilogram of body weight, and it is found that this antibody can significantly reduce the serious degree of hepatic adipose infiltration and reduce serum TG (triglyceride) level. We further prepared the anti-human FAM3B polyclonal antibody, the monoclonal antibody and the single-strand antibody, and humanization for this antibody is carried out. The investigations on the reduction of serious degree of hepatic adipose infiltration and reduction in various kinds of blood-fat indexes by using humanized monoclonal antibody and single-strand antibody had been carried out in animals.

Example 10

Establishment of Hyperlipemia Model in Mice

The hyperlipemia model of mice is induced by using high-fat feeds, the C57BL/6J mice are purchased from Vital River, male, three weeks old. The formula for the high fat feeds is as below: basic feeds 83.5%, pork fat 12%, 1% cholesterol, 10% pork fat, 0.2% propylthiouracil, 0.3% sodium deoxycholate, 5% sucrose, and it is produced by the experimental animal center of Academy of Military Medical Sciences. The hyperlipemia model of mice is obtained after induction for 3-4 weeks.

Example 11

Inhibition on FAM3B Protein Expression in Hepatic Tissues by the Small Interfering Nucleotide for FAM3B Gene After the small interfering nucleotide of FAM3B gene FAM3B-46 is labelled with cholesterol or coated with liposome, it is injected into the hyperlipemia model of mice via their tail veins. The injection is carried out for continuous 7 days with one injection each day and the samples are collected after 7 days. The standard dosages for injection are 2.5 mg, 5 mg and 10 mg for every kilogram of body weight. Other dosages such as 0.1 mg-50 mg small interfering nucleotide for every kilogram of body weight are also under test. The small interfering nucleotide in standard dosages can reduce FAM3B protein expression in hepatic tissues by 40%, while the unrelated small interfering nucleotide to FAM3B in the control could not significantly reduce FAM3B protein expression in hepatic tissues.

Example 11

Inhibition on FAM3B mRNA Expression in Intestine by the Small Interfering Nucleotide for FAM3B Gene After the small interfering nucleotide of FAM3B gene FAM3B-46 is labelled with cholesterol or coated with liposome, it is injected into the hyperlipemia model of mice via their tail veins. The injection is carried out for continuous 7 days with one injection each day and the samples are collected after 7 days. The standard dosages for injection are 2.5 mg, 5 mg and 10 mg for every kilogram of body weight. Other dosages such as 0.1 mg-50 mg small interfering nucleotide for every kilogram of body weight are also under test. The small interfering nucleotide in standard dosages can reduce FAM3B mRNA expression in intestine by 45%, while the unrelated small interfering nucleotide to FAM3B in the control could not significantly reduce FAM3B mRNA expression in intestine. The results are shown in FIG. 7.

Example 12

Inhibition on FAM3B mRNA Expression in Intestine by the Small Interfering Nucleotide for FAM3B Gene After the small interfering nucleotide of FAM3B gene FAM3B-46 is labelled with cholesterol or coated with liposome, it is injected into the hyperlipemia model of mice via their tail veins. The injection is carried out for continuous 7 days with one injection each day and the samples are collected after 7 days. The standard dosages for injection are 2.5 mg, 5 mg and 10 mg for every kilogram of body weight. Other dosages such as 0.1 mg-50 mg small interfering nucleotide for every kilogram of body weight are also under test. The small interfering nucleotide in standard dosages can reduce FAM3B protein expression in intestine by 30%, while the unrelated small interfering nucleotide to FAM3B in the control could not significantly reduce FAM3B protein expression in intestine.

Example 13

Inhibition on TG and Cholesterol Levels in Hepatic Tissues by the Small Interfering Nucleotide for FAM3B Gene After the small interfering nucleotide of FAM3B gene FAM3B-46 is labelled with cholesterol or coated with liposome, it is injected into the hyperlipemia model of mice via their tail veins. The injection is carried out for continuous 7 days with one injection each day and the samples are collected after 7 days. The standard dosages for injection are 2.5 mg, 5 mg and 10 mg for every kilogram of body weight. Other dosages such as 0.1 mg-50 mg small interfering nucleotide for every kilogram of body weight are also under test. The products from Zhongsheng Beikong Biological Technological Co., Ltd. are used as the kit for detecting triglyceride (TG) and cholesterol, and they are determined on a SABA/18 automated biochemical analyzer. The detections are carried out with reference to the instruction for the kits of Biosino Bio-Technology and Science Incorporation. The animals are subjected to fast dieting 16 hours before blood sample collection. The small interfering nucleotide in a dosage of 5 mg and 10 mg/kilogram body weight can reduce TG level in hepatic tissues by 20-40%, while the unrelated small interfering nucleotide to FAM3B in the control could not significantly reduce the TG level in hepatic tissues. Simultaneously, the cholesterol level in hepatic tissues is also examined, and the results showed that the small interfering nucleotide in a dosage of 10 mg/kilogram body weight can reduce cholesterol level in hepatic tissues by 15-30%, while the unrelated small interfering nucleotide to FAM3B in the control could not significantly reduce the cholesterol level in hepatic tissues. The results are shown in FIG. 8.

Example 14

Inhibition on TG and Cholesterol Levels in the Blood by Using the Small Interfering Nucleotide for FAM3B Gene After the small interfering nucleotide of FAM3B gene FAM3B-46 is labelled with cholesterol or coated with liposome, it is injected into the hyperlipemia model of mice via their tail veins. The injection is carried out for continuous 7 days with one injection each day and the samples are collected after 7 days. The standard dosages for injection are 2.5 mg, 5 mg and 10 mg for every kilogram of body weight. Other dosages such as 0.1 mg-50 mg small interfering nucleotide for every kilogram of body weight are also under test. The small interfering nucleotide in standard dosages and a dosage of 10 mg/kilogram body weight can reduce TG level in blood by 25-50%, while the unrelated small interfering nucleotide to FAM3B in the control could not significantly reduce the TG level in blood. Simultaneously, the cholesterol level in blood is also examined, and the results showed that the small interfering nucleotide in standard dosages and a dosage of 10 mg/kilogram body weight can reduce cholesterol level in hepatic tissues by 25-50%, while the unrelated small interfering nucleotide to FAM3B in the control could not significantly reduce the cholesterol level in blood. The results are shown in FIG. 9.

TABLE 1

| Serial number | | Sequence of the small interfering nucleotide | Range of attacking Target | |
|---|---|---|---|---|
| FAM3B-1 | sense strand | 5'-GCCUGCUCAAGGUGGUGUUdTdT-3' | 166-184 | SEQ ID NO: 45 |
| | antisense strand | 5'-AACACCACCUUGAGCAGGCdTdT-3' | | |
| FAM3B-2 | sense strand | 5'-UUCGUGGUCUUCGCCUCCUUGdTdT-3' | 183-203 | SEQ ID NO: 46 |
| | antisense strand | 5'-CAAGGAGGCGAAGACCACGAAdTdT-3' | | |
| FAM3B-3 | sense strand | 5'-CCUGCUCGCAGAGCUCAUUdTdT-3' | 224-242 | SEQ ID NO: 47 |
| | antisense strand | 5'-AAUGAGCUCUGCGAGCAGGdTdT-3' | | |
| FAM3B-4 | sense strand | 5'-CCAGUGCUGCCUAUAGCAUdTdT-3' | 259-277 | SEQ ID NO: 48 |
| | antisense strand | 5'-AUGCUAUAGGCAGCACUGGdTdT-3' | | |
| FAM3B-5 | sense strand | 5'-UGACACCUAUGCCUACAGGUUdTdT-3' | 359-379 | SEQ ID NO: 49 |
| | antisense strand | 5'-AACCUGUAGGCAUAGGUGUCAdTdT-3' | | |
| FAM3B-6 | sense strand | 5'-UACAGGUUACUCAGCGGAGGUdTdT-3' | 372-392 | SEQ ID NO: 50 |
| | antisense strand | 5'-ACCUCCGCUGAGUAACCUGUAdTdT-3' | | |
| FAM3B-7 | sense strand | 5'-AUCUGCUUUGAGGAUAACCUAdTdT-3' | 414-434 | SEQ ID NO: 51 |
| | antisense strand | 5'-UAGGUUAUCCUCAAAGCAGAUdTdT-3' | | |
| FAM3B-8 | sense strand | 5'-UGGGAGAACAGCUGGGAAAdTdT-3' | 439-457 | SEQ ID NO: 52 |
| | antisense strand | 5'-UUUCCCAGCUGUUCUCCCAdTdT-3' | | |
| FAM3B-9 | sense strand | 5'-GGAAAUGUUGCCAGAGGAAdTdT-3' | 453-471 | SEQ ID NO: 53 |
| | antisense strand | 5'-UUCCUCUGGCAACAUUUCCdTdT-3' | | |
| FAM3B-10 | sense strand | 5'-GCCAUUGUCAACUAUGUAAdTdT-3' | 480-498 | SEQ ID NO: 54 |
| | antisense strand | 5'-UUACAUAGUUGACAAUGGCdTdT-3' | | |

TABLE 1-continued

| Serial number | | Sequence of the small interfering nucleotide | Range of attacking | Target |
|---|---|---|---|---|
| FAM3B-11 | sense strand | 5'-CUCUGGACCGAUGACAAAGdTdT-3' | 548-568 | SEQ ID NO: 55 |
| | antisense strand | 5'-CUUUGUCAUCGGUCCAGAGdTdT-3' | | |
| FAM3B-12 | sense strand | 5'-GCUCUUCAUGGUGACCUAUdTdT-3' | 596-614 | SEQ ID NO: 56 |
| | antisense strand | 5'-AUAGGUCACCAUGAAGAGCdTdT-3' | | |
| FAM3B-13 | sense strand | 5'-GCACAAGACUGAAUAACGAdTdT-3' | 625-643 | SEQ ID NO: 57 |
| | antisense strand | 5'-UCGUUAUUCAGUCUUGUGCdTdT-3' | | |
| FAM3B-14 | sense strand | 5'-GCCAUAGAAGCACUUGGAAdTdT-3' | 654-672 | SEQ ID NO: 58 |
| | antisense strand | 5'-UUCCAAGUGCUUCUAUGGCdTdT-3' | | |
| FAM3B-15 | sense strand | 5'-GCACUUGGAAGUAAAGAAAdTdT-3' | 663-681 | SEQ ID NO: 59 |
| | antisense strand | 5'-UUUCUUUACUUCCAAGUGCdTdT-3' | | |
| FAM3B-16 | sense strand | 5'-AGUAAAGAAAUCAGGAACAdTdT-3' | 672-690 | SEQ ID NO: 60 |
| | antisense strand | 5'-UGUUCCUGAUUUCUUUACUdTdT-3' | | |
| FAM3B-17 | sense strand | 5'-GGUCUAGCUGGGUAUUUAUdTdT-3' | 700-718 | SEQ ID NO: 61 |
| | antisense strand | 5'-AUAAAUACCCAGCUAGACCdTdT-3' | | |
| FAM3B-18 | sense strand | 5'-UCCGAAAUUCAGAGAGAAAdTdT-3' | 744-762 | SEQ ID NO: 62 |
| | antisense strand | 5'-UUUCUCUCUGAAUUUCGGAdTdT-3' | | |
| FAM3B-19 | sense strand | 5'-GAUCAACCACUCUGAUGCUdTdT-3' | 764-784 | SEQ ID NO: 63 |
| | antisense strand | 5'-AGCAUCAGAGUGGUUGAUCdTdT-3' | | |
| FAM3B-20 | sense strand | 5'-GCUAAGAACAACAGAUAUUdTdT-3' | 780-798 | SEQ ID NO: 64 |
| | antisense strand | 5'-AAUAUCUGUUGUUCUUAGCdTdT-3' | | |
| FAM3B-21 | sense strand | 5'-CUGCAGAGAUCCAGAUAGAdTdT-3' | 808-826 | SEQ ID NO: 65 |
| | antisense strand | 5'-UCUAUCUGGAUCUCUGCAGdTdT-3' | | |
| FAM3B-22 | sense strand | 5'-CCAGAUAGAAGGCUGCAUAdTdT-3' | 818-836 | SEQ ID NO: 66 |
| | antisense strand | 5'-UAUGCAGCCUUCUAUCUGGdTdT-3' | | |
| FAM3B-23 | sense strand | 5'-CUGCAUACCCAAAGAACGAdTdT-3' | 830-848 | SEQ ID NO: 67 |
| | antisense strand | 5'-UCGUUCUUUGGGUAUGCAGdTdT-3' | | |
| FAM3B-24 | sense strand | 5'-GAGUAAAUGUGUUCUGUAUdTdT-3' | 869-887 | SEQ ID NO: 68 |
| | antisense strand | 5'-AUACAGAACACAUUUACUCdTdT-3' | | |
| FAM3B-25 | sense strand | 5'-AAACAAAUGCAGCUGGAAUdTdT-3' | 888-906 | SEQ ID NO: 69 |
| | antisense strand | 5'-AUUCCAGCUGCAUUUGUUUdTdT-3' | | |

TABLE 1-continued

| Serial number | | Sequence of the small interfering nucleotide | Range of attacking | Target |
|---|---|---|---|---|
| FAM3B-26 | sense strand | 5'-GCCCAUAUUUGAUGAGUAUdTdT-3' | 939-957 | SEQ ID NO: 70 |
| | antisense strand | 5'-AUACUCAUCAAAUAUGGGCdTdT-3' | | |
| FAM3B-27 | sense strand | 5'-GUUGUAAACCAAUGAACAUdTdT-3' | 967-985 | SEQ ID NO: 71 |
| | antisense strand | 5'-AUGUUCAUUGGUUUACAACdTdT-3' | | |
| FAM3B-28 | sense strand | 5'-GUAGUGAAGAUGUCAAUUAdTdT-3' | 1038-1056 | SEQ ID NO: 72 |
| | antisense strand | 5'-UAAUUGACAUCUUCACUACdTdT-3' | | |
| FAM3B-29 | sense strand | 5'-GAUGUCAAUUAGCAGGAAAdTdT-3' | 1046-1064 | SEQ ID NO: 73 |
| | antisense strand | 5'-UUUCCUGCUAAUUGACAUCdTdT-3' | | |
| FAM3B-30 | sense strand | 5'-GCAGGAAACUAAAAUGAAUdTdT-3' | 1057-1075 | SEQ ID NO: 74 |
| | antisense strand | 5'-AUUCAUUUUAGUUUCCUGCdTdT-3' | | |
| FAM3B-31 | sense strand | 5'-GAAAGAGGGUUGGGAGAAAdTdT-3' | 1111-1129 | SEQ ID NO: 75 |
| | antisense strand | 5'-UUUCUCCCAACCCUCUUUCdTdT-3' | | |
| FAM3B-32 | sense strand | 5'-AGACAGCCCUGCAGAGAGAdTdT-3' | 1189-1207 | SEQ ID NO: 76 |
| | antisense strand | 5'-UCUCUCUGCAGGGCUGUCUdTdT-3' | | |

The said range of attacking referred to the position of complementary binding between the antisense strand of the small interfering nucleotide and SEQ ID NO:1.

TABLE 2

| Serial number | | Sequence of the small interfering nucleotide | Range of attacking | Target |
|---|---|---|---|---|
| FAM3B-33 | Sense strand | 5'-UCCAGGAACAGAUAUGCAGdTdT-3' | 732-750 | SEQ ID NO: 80 |
| | antisense strand | 5'-CUGCAUAUCUGUUCCUGGAdTdT-3' | | |
| FAM3B-34 | sense strand | 5'-AUCAACCACUCAGAUCAAUdTdT-3' | 714-732 | SEQ ID NO: 81 |
| | antisense strand | 5'-AUUGAUCUGAGUGGUUGAUdTdT-3' | | |
| FAM3B-35 | sense strand | 5'-CCAGCACUCUCUACAACAUdTdT-3' | 208-226 | SEQ ID NO: 82 |
| | antisense strand | 5'-AUGUUGUAGAGAGUGCUGGdTdT-3' | | |
| FAM3B-36 | sense strand | 5'-GCCGCGACAAGUAUGCCAAdTdT-3' | 462-480 | SEQ ID NO: 83 |
| | antisense strand | 5'-UUGGCAUACUUGUCGCGGCdTdT-3' | | |
| FAM3B-37 | sense strand | 5'-GCCAAUGGCCAAGUUCAUUdTdT-3' | 503-521 | SEQ ID NO: 84 |
| | antisense strand | 5'-AAUGAACUUGGCCAUUGGCdTdT-3' | | |
| FAM3B-38 | sense strand | 5'-GCCAUAGAAGCCCUUGGAAdTdT-3' | 603-621 | SEQ ID NO: 85 |
| | antisense strand | 5'-UUCCAAGGGCUUCUAUGGCdTdT-3' | | |

TABLE 2-continued

| Serial number | Sequence of the small interfering nucleotide | Range of attacking Target | |
|---|---|---|---|
| FAM3B-39 sense strand | 5'-GCAAAGAAAUCAAGAACAUdTdT-3' | 622-640 | SEQ ID NO: 86 |
| antisense strand | 5'-AUGUUCUUGAUUUCUUUGCdTdT-3' | | |
| FAM3B-40 sense strand | 5'-GAAUGUGGCAAGAGGGAUAdTdT-3' | 404-422 | SEQ ID NO: 87 |
| antisense strand | 5'-UAUCCCUCUUGCCACAUUCdTdT-3' | | |
| FAM3B-41 sense strand | 5'-UCAGAAAUCGAGAGAGAAAdTdT-3' | 693-711 | SEQ ID NO: 88 |
| antisense strand | 5'-UUUCUCUCUCGAUUUCUGAdTdT-3' | | |
| FAM3B-42 sense strand | 5'-CCGAAGCAUUGGAGAGAGAdTdT-3' | 227-245 | SEQ ID NO: 89 |
| antisense strand | 5'-UCUCUCUCCAAUGCUUCGGdTdT-3' | | |

The said range of attacking referred to the position of complementary binding between the antisense strand of small interfering nucleotide and SEQ ID NO:44.

TABLE 3

| Serial number | Modification | |
|---|---|---|
| FAM3B-43 | 5-GCCAUAGAAGCCCUUGGAAdTdT | (SEQ ID NO: 39) |
| | 5-UUCCAAGGGCUUCUAUGGCdTdT | (SEQ ID NO: 85) |
| FAM3B-44 | 5-CCGAAGCAUUGGAGAGAGAdTdT | (SEQ ID NO: 43) |
| | 5-UCUCUCUCCAAUGCUUCGGdTdT | (SEQ ID NO: 89) |
| FAM3B-45 | 5-CCAGCACUCUCUACAACAUdTdT | (SEQ ID NO: 36) |
| | 5-AUGUUGUAGAGAGUGCUGGdTdT | (SEQ ID NO: 82) |
| FAM3B-46 | 5-UCAGAAAUCGAGAGAGAAAdTdT | (SEQ ID NO: 42) |
| | 5-UUUCUCUCUCGAUUUCUGAdTdT | (SEQ ID NO: 88) |

Note:
the italic indicated OM modification, F modification, thio-modification or cholesterol modification.

FIG. 1 showed the in vitro screening results for active targets in FAM3B by using 10 mouse-derived small interfering nucleotides in the present invention. It can be found from FIG. 1 that FAM3B-33 to FAM3B-42 have relatively high inhibitory activities on FAM3B gene, particularly the inhibitory activities of the small interfering nucleotides FAM3B-34, FAM3B-35, FAM3B-38, FAM3B-39, FAM3B-40, FAM3B-41 and FAM3B-42 on FAM3B gene are as high as 80-97% respectively.

FIG. 2 showed the oil red O and HE staining results for the degree of hepatic adipose infiltration in the mice after they are intravenously administered with FAM3B-46 in the present invention. It can be found from FIG. 2 that the serious degree of hepatic adipose infiltration is significantly reduced 15 days after the intravenous administration with FAM3B-46, and it showed good dose-dependent manner to the dosage of pharmaceutical administration.

FIG. 3 showed the results for the inhibitory effects of FAM3B-43 to FAM3B-46 in the present invention on FAM3B mRNA expression in hepatic tissues after intravenous pharmaceutical administration. It can be found from FIG. 3 that the small interfering nucleotides FAM3B-43 to FAM3B-46 in the present invention can significantly inhibit FAM3B gene expression in hepatic tissues in the mice.

FIG. 4 showed the results from the detection on the in vitro inhibitory effects of human derived from FAM3B-1 to FAM3B-32 in the present invention on FAM3B mRNA expression in the cells. It can be seen from FIG. 4 that the small interfering nucleotides from FAM3B-1 to FAM3B-32 can significantly inhibit FAM3B gene expression in HepG2 cells, particularly the inhibitory rates of the small interfering nucleotides FAM3B-20, FAM3B-11, FAM3B-24, FAM3B-15 and FAM3B-17 on FAM3B mRNA expression in HepG2 cells are higher than 80%.

FIG. 5 showed the results from the detection on the in vitro inhibitory effects of the small interfering nucleotides in the present invention on FAM3B protein expression in the cells. It can be seen from FIG. 5 that the small interfering nucleotides FAM3B-20, FAM3B-11, FAM3B-24, FAM3B-15 and FAM3B-17 can significantly inhibit FAM3B protein level in HepG2 cells and the inhibitory rates are higher than 80%.

FIG. 6 showed the results from the detection on the in vitro inhibitory effects of the small interfering nucleotides in the present invention on induced fatty deposition in HepG2 cells. It can be found from FIG. 6 that the small interfering nucleotide in the present invention FAM3B-20 can significantly inhibit fatty deposition in HepG2 cells.

FIG. 7 showed the results from the detection on the inhibitory effects of the small interfering nucleotide in the present invention on intestinal FAM3B mRNA expression in the mice after intravenous administration with FAM3B-46. It can be found from FIG. 7 that the small interfering nucleotide in the present invention FAM3B-46 can significantly inhibit intestinal FAM3B gene expression in the mice and the dose-dependent manner is good.

FIG. 8 showed the results from the detection on TG and cholesterol levels in hepatic tissues in the mice after intravenous administration with FAM3B-46 in different dosages. It can be found from FIG. 8 that the small interfering nucleotide FAM3B-46 can significantly reduce TG and cholesterol levels in hepatic tissues of the mice and the inhibitory effects on TG level showed relatively good dose-dependent manner.

FIG. 9 showed the results from the detection on TG and cholesterol levels in blood in the mice after intravenous administration with FAM3B-46 in different dosages. It can be found from FIG. 9 that the small interfering nucleotide FAM3B-46 can significantly reduce TG and cholesterol levels in blood of the mice and the inhibitory effects showed relatively good dose-dependent manner.

It can be found from the results as mentioned above that the inhibitor in the present invention can be effectively utilized for preventing and/or treating the diseases mediated by FAM3B gene expression, such as hepatic adipose infiltration and diseases induced by hyperlipemia.

The invention claimed is:

1. A siRNA, characterized in that, the nucleotide sequence of the siRNA comprises the nucleotide sequence shown as FAM3B-11, or the nucleotide sequence of the siRNA comprises modified products of the nucleotide sequence shown as FAM3B-11, wherein,

```
FAM3B-11
sense strand:
                                           (SEQ ID No: 12)
              5'- CUCUGGACCGAUGACAAAGdTdT-3' antisense strand:
                                           (SEQ ID No: 55)
              5'- CUUUGUCAUCGGUCCAGAGdTdT-3'.
```

2. An inhibitor composition, characterized in that, the inhibitor composition comprises the siRNA according to any one of claim 1, as the active ingredient.

3. A method for preventing and/or treating the disease mediated by FAM3B gene expression, characterized in that, the method comprises inhibiting FAM3B gene expression in patients to reduce the level of FAM3B gene expression by administering the siRNA according to claim 1 or the inhibitor composition according to claim 2 to the patients.

4. The method according to claim 3, wherein, the disease mediated by FAM3B gene expression is hepatic adipose infiltration or the disease induced by hyperlipemia.

5. The method according to claim 4, wherein blood fat of hyperlipemia of the patients is serum triglyceride and/or cholesterol.

6. A method of preparing small interfering RNA suitable for preventing and/or treating disease mediated by FAM 3B gene expression comprising modifying the siRNA according to claim 1; and assessing the modified siRNA for inhibitory activity associated with FAM3B gene expression.

7. The method according to claim 6, wherein, the disease is hepatic adipose infiltration or the disease induced by hyperlipemia.

8. The method according to claim 7, wherein blood fat of hyperlipemia is serum triglyceride and/or cholesterol.

* * * * *

SEQUENCE LISTING

<160> NUMBER OF SEQ ID NOS: 89

<210> SEQ ID NO 1
<211> LENGTH: 1384
<212> TYPE: DNA
<213> ORGANISM: Homo sapiens
<220> FEATURE:
<223> OTHER INFORMATION: FAM3B

<400> SEQUENCE: 1

| | | | | | |
|---|---|---|---|---|---|
| tttgcccgac | tggccgcgca | cccagctggc | ccgcccctgc | ccgacacgac | cgctgcccgc | 60 |
| cccttgcctt | cctgacccag | gggctccgct | ggctgcggtc | gcctgggagc | tgccgccagg | 120 |
| gccaggaggg | gagcggcacc | tggaagatgc | gcccattggc | tggtggcctg | ctcaaggtgg | 180 |
| tgttcgtggt | cttcgcctcc | ttgtgtgcct | ggtattcggg | gtacctgctc | gcagagctca | 240 |
| ttccagatgc | acccctgtcc | agtgctgcct | atagcatccg | cagcatcggg | gagaggcctg | 300 |
| tcctcaaagc | tccagtcccc | aaaaggcaaa | aatgtgacca | ctggactccc | tgcccatctg | 360 |
| acacctatgc | ctacaggtta | ctcagcggag | gtggcagaag | caagtacgcc | aaaatctgct | 420 |
| ttgaggataa | cctacttatg | ggagaacagc | tgggaaatgt | tgccagagga | ataaacattg | 480 |
| ccattgtcaa | ctatgtaact | gggaatgtga | cagcaacacg | atgttttgat | atgtatgaag | 540 |
| gtgataactc | tggaccgatg | acaaagttta | ttcagagtgc | tgctccaaaa | tccctgctct | 600 |
| tcatggtgac | ctatgacgac | ggaagcacaa | gactgaataa | cgatgccaag | aatgccatag | 660 |
| aagcacttgg | aagtaaagaa | atcaggaaca | tgaaattcag | gtctagctgg | gtatttattg | 720 |
| cagcaaaagg | cttggaactc | ccttccgaaa | ttcagagaga | aaagatcaac | cactctgatg | 780 |
| ctaagaacaa | cagatattct | ggctggcctg | cagagatcca | gatagaaggc | tgcataccca | 840 |
| aagaacgaag | ctgacactgc | agggtcctga | gtaaatgtgt | tctgtataaa | caaatgcagc | 900 |
| tggaatcgct | caagaatctt | attttctaa | atccaacagc | ccatatttga | tgagtatttt | 960 |
| gggtttgttg | taaaccaatg | aacatttgct | agttgtatca | aatcttggta | cgcagtattt | 1020 |
| ttataccagt | attttatgta | gtgaagatgt | caattagcag | gaaactaaaa | tgaatggaaa | 1080 |
| ttcttaaagg | gaatgatgtg | attcaagctg | gaaagagggt | tgggagaaac | agcttgtcca | 1140 |
| ggtggagcta | tgttatgatc | agatcgaagt | gtgacccctg | tgtggtccag | acagccctgc | 1200 |
| agagagaaaa | cctttattcc | attatcacca | agcacctcct | agtttccgac | agtcatctcc | 1260 |
| ttctgctggg | agaattagca | gcagttcagg | gggcttatgt | tatgtccttg | ttcaactcaa | 1320 |
| cttgagctct | tgaactcctc | ctgtgggcct | gtgaatgtat | tcattcattc | cacaactctg | 1380 |
| ggtg | | | | | | 1384 |

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<223> OTHER INFORMATION: FAM3B gene mRNA

<400> SEQUENCE: 2
gccugcucaa ggugguguut t                                              21

-continued

```
<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 3
uucguggucu ucgccuccuu gtt                                               23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 4
ccugcucgca gagcucauut t                                                 21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 5
ccagugcugc cuauagcaut t                                                 21

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 6
ugacaccuau gccuacaggu utt                                               23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 7
uacagguuac ucagcggagg utt                                               23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 8
aucugcuuug aggauaaccu att                                               23

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 9
ugggagaaca gcugggaaat t                                                 21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 10
ggaaauguug ccagaggaat t                                                 21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 11
```

-continued gccauuguca acuauguaat t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 12
cucuggaccg augacaaagt t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 13
gcucuucaug gugaccuaut t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 14
gcacaagacu gaauaacgat t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 15
gccauagaag cacuuggaat t                                              21

<210> SEQ ID NO 16
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 16
gcacuuggaa guaaagaaat t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 17
aguaaagaaa ucaggaacat t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 18
ggucuagcug gguauuuaut t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 19
uccgaaauuc agagagaaat t                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA -continued

```
<400> SEQUENCE: 20
gaucaaccac ucugaugcut t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 21
gcuaagaaca acagauauut t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 22
cugcagagau ccagauagat t                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 23
ccagauagaa ggcugcauat t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 24
cugcauaccc aaagaacgat t                                              21

<210> SEQ ID NO 25
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 25
gaguaaaugu guucuguaut t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 26
aaacaaaugc agcuggaaut t                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 27
gcccauauuu gaugaguaut t                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 28
guuguaaacc aaugaacaut t                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
```

```
<223> OTHER INFORMATION: FAM3B gene mRNA

<400> SEQUENCE: 29
guagugaaga ugucaauuat t                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 30
gaugucaauu agcaggaaat t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 31
gcaggaaacu aaaugaaut t                                               21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 32
gaaagagggu ugggagaaat t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 33
agacagcccu gcagagagat t                                              21

<210> SEQ ID NO 34
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 34
uccaggaaca gauaugcagt t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 35
aucaaccacu cagaucaaut t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 36
ccagcacucu cuacaacaut t                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 37
gccgcgacaa guaugccaat t                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

```
        Synthetic oligonucleotide
<220> FEATURE:
<223> OTHER INFORMATION: FAM3B gene mRNA

<400> SEQUENCE: 38
gccaauggcc aaguucauut t                                               21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 39
gccauagaag cccuuggaat t                                               21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 40
gcaaagaaau caagaacaut t                                               21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 41
gaauguggca agagggauat t                                               21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 42
ucagaaaucg agagagaaat t                                               21
```

-continued

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: FAM3B gene mRNA

<400> SEQUENCE: 43
ccgaagcauu ggagagagat t                                              21

<210> SEQ ID NO 44
<211> LENGTH: 871
<212> TYPE: DNA
<213> ORGANISM: Mus musculus
<220> FEATURE:
<223> OTHER INFORMATION: FAM3B gene mRNA

<400> SEQUENCE: 44
ataatctatg tgcagctcaa gcaggtaggc cagctttcat aggtccctgg ggattgcagc     60
caagagctga gtagaaagag agcagtttct ggaagatgcg tccagttgct acaggcatct    120
tcaaggcact agtgtttatt ttctcctccc tgtgcgcctg gtattctggg tacctgctcg    180
cggagctcat tcctgacgtg ccctgtcca gcactctcta caacatccga agcattggag    240
agagacctgt tctcaaagcc ccagccccca aaagacaaaa atgtgaccat tggtccccat    300
gtcctcctga cacctatgcc taccggctgc tcagtggtgg tggccgcgac aagtatgcca    360
agatctgctt tgaggatgaa gtgctaatag gagagaagac ggggaatgtg gcaagaggga    420
taaacattgc tgtcgtcaac tatgagacag gaaaagtgat agcgacaaag tactttgata    480
tgtatgaagg tgataactcc gggccaatgg ccaagttcat tcagagcact ccttcaaaat    540
ccctgctgtt catggtgact catgatgatg gaagttccaa actgaaggct caagcaaagg    600
atgccataga agcccttgga agcaaagaaa tcaagaacat gaagttcaga tcaagctggg    660
tgtttgttgc agcaaagggc tttgagctcc cttcagaaat cgagagagaa aaaatcaacc    720
actcagatca atccaggaac agatatgcag gctggccagc ggagatccag atcgaaggat    780
gcatacccaa agggctgaga taacggtgct tggacctcaa taaacacgtt ttgtacagat    840
atactcagct ggaaaaaaaa aaaaaaaaa a                                    871

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 45
aacaccaccu ugagcaggct t                                              21

<210> SEQ ID NO 46
<211> LENGTH: 23
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 46
caaggaggcg aagaccacga att                                            23

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 47
aaugagcucu gcgagcaggt t                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 48
augcuauagg cagcacuggt t                                              21

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 49
aaccuguagg cauagguguc att                                            23

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 50
accuccgcug aguaaccugu att                                            23

<210> SEQ ID NO 51
<211> LENGTH: 23
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 51
uagguuaucc ucaaagcaga utt                                              23

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 52 uucccagcu guucucccat t                                                 21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53
uuccucuggc aacauuucct t                                                21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 54
uuacauaguu gacaauggct t                                                21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 55
cuuugucauc gguccagagt t                                                21

<210> SEQ ID NO 56
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 56
auaggucacc augaagagct t                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 57
ucguuauuca gucuugugct t                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 58 uuccagugc uucuauggct t                                               21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 59
uuucuuuacu uccaagugct t                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 60
uguuccugau uucuuuacut t                                              21

<210> SEQ ID NO 61
<211> LENGTH: 21
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 61
auaaauaccc agcuagacct t                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 62
uuucucucug aauuucggat t                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 63
agcaucagag ugguugauct t                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 64
aauaucuguu guucuuagct t                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 65
ucuaucugga ucucugcagt t                                              21

<210> SEQ ID NO 66
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 66
uaugcagccu ucuaucuggt t                                                    21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 67
ucguucuuug gguaugcagt t                                                    21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 68
auacagaaca cauuuacuct t                                                    21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 69
auuccagcug cauuuguuut t                                                    21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 70
auacucauca aauaugggct t                                                    21

<210> SEQ ID NO 71
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 71
auguucauug guuuacaact t                                                    21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 72
uaauugacau cuucacuact t                                                    21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 73
uuuccugcua auugacauct t                                                    21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 74
auucauuuua guuccugct t                                                     21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 75
uuucucccaa cccucuuuct t                                                    21

<210> SEQ ID NO 76
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 76
ucucucugca gggcugucut t                                                   21

<210> SEQ ID NO 77
<211> LENGTH: 12
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 77 tttttggaa tt                                                              12

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 78
uucuccgaac gugucacgut t                                                   21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 79
acgugacacg uucggagaat t                                                   21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 80
cugcauaucu guuccuggat t                                                   21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide

<400> SEQUENCE: 81
auugaucuga gugguugaut t                                              21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 82 auuuguaga gagugcuggt t                                               21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 83
uuggcauacu ugucgcggct t                                              21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 84
aaugaacuug gccauuggct t                                              21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 85
uuccaagggc uucuauggct t                                              21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

-continued

```
<223> OTHER INFORMATION: Description of Combined DNA/RNA Molecule:
      Synthetic oligonucleotide

<400> SEQUENCE: 86
auguucuuga uuucuuugct t                                              21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 87
uaucccucuu gccacauuct t                                              21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 88
uuucucucuc gauuucugat t                                              21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 89
ucucucucca augcuucggt t                                              21
```